United States Patent [19]

Trachtman

[11] Patent Number: 5,002,384
[45] Date of Patent: * Mar. 26, 1991

[54] METHODS AND APPARATUS FOR MONITORING AND TRAINING EYE POSITION

[76] Inventor: Joseph N. Trachtman, 57 Hicks St., Brooklyn, N.Y. 11201

[ * ] Notice: The portion of the term of this patent subsequent to Aug. 6, 2002 has been disclaimed.

[21] Appl. No.: 1,337

[22] Filed: Jan. 7, 1987

Related U.S. Application Data

[63] Continuation-in-part of Ser. No. 829,555, Feb. 13, 1986, Pat. No. 4,660,945, which is a continuation of Ser. No. 716,025, Mar. 25, 1985, abandoned, which is a continuation of Ser. No. 460,850, Jan. 25, 1983, Pat. No. 4,533,221.

[51] Int. Cl.$^5$ ............................................. A61B 3/00
[52] U.S. Cl. ................................. 351/203; 351/210
[58] Field of Search .............. 351/203, 209, 210, 208, 351/211

[56] References Cited

U.S. PATENT DOCUMENTS

| | | | |
|---|---|---|---|
| 3,679,295 | 7/1972 | Newman et al. | 351/210 |
| 3,986,030 | 10/1976 | Teltscher | 351/210 |
| 4,533,221 | 8/1985 | Trachtman | 351/203 |
| 4,660,945 | 4/1987 | Trachtman | 351/208 |

*Primary Examiner*—Paul M. Dzierzynski
*Attorney, Agent, or Firm*—Marvin S. Gittes

[57] ABSTRACT

Methods and apparatus for monitoring and training eye position under clinical conditions are provided in accordance with the teachings of the present invention. An infrared optometer is employed to measure a patient's corneal and retinal reflection and outputs therefrom are employed to generate tone information and viewable patient information indicative of eye position and the state of focus. A patient is trained until a predetermined proficiency in the voluntary control of eye position is achieved.

17 Claims, 3 Drawing Sheets

METHODS AND APPARATUS FOR MONITORING AND TRAINING EYE POSITION

This application is a continuation-in-part of U.S. application Ser. No. 829,555, filed Feb. 13, 1986, now U.S. Pat. No. 4,660,945, which was a continuation of U.S. application Ser. No. 716,025, filed Mar. 25, 1985, now abandoned, which was a continuation of U.S. application Ser. No. 460,850 filed Jan. 25, 1983, now U.S. Pat. No. 4,533,221.

This continuation-in-part relates to methods and apparatus for monitoring and training eye position and more particularly to methods and apparatus for treating and correcting, through training, strabismus, nystagmus, eccentric fixation and other related disorders of the eye.

BACKGROUND OF THE INVENTION

It has been demonstrated that voluntary control of accommodation may be acquired by experimental emmetropic subjects under laboratory conditions through the use of biofeedback techniques. This has been reported by T. N. Cornsweet and H. D. Crane in their Research Note entitled "Training the Visual Accommodation System" published in VISION RES., Vol. 13, pp. 713–715, Pergamon Press 1973, as printed in Great Britain. Similar results have also been reported by R. J. Randle in "Volitional Control of Visual Accommodation", Advisory Group for Aerospace Res. and Dev. (AGARD), CONF. PROC. 82. Carmisch-Partenkirchen, Germany, 15–17 Sept. 1970.

This is perhaps not surprising when analyzed in retrospect, because the focusing or ciliary muscle which is attached by zonules to the crystalline lens of the eye and controls the thickness and thinness thereof to achieve focus, is a sphincter or ring muscle of approximately 2 millimeters located directly behind the iris. The ciliary muscle contracts to make the lens thicken when something close is viewed and this muscle dilates to make the lens thinner when objects are viewed at a distance. The ciliary muscle is also controlled by that part of the nervous system that controls heart rate, body temperature, breathing, blood pressure, stomach acidity and bowel motility, and under conditions of stress the ciliary muscle will undergo spasm causing a myopic condition. Thus, given the normal vision and functions of the ciliary muscle in focusing an image on the retina in an experimental emmetropic subject and the provision of biofeedback indicative of the state of the experimental subject's accommodation, it is reasonable to expect that voluntary control of the ciliary muscle, and hence, of accommodation may be learned in a manner similar to the control of other functions governed by this portion of the nervous system as obtained, for example, through disciplines such as transcendental meditation, yoga and the like.

The application of voluntary control of accommodation to reduce limited functional myopia has also been the subject of experimentation as reported in "Biofeedback of Accommodation to Reduce Functional Myopia: A Case Report" by Joseph N. Trachtman in THE AMERICAN JOURNAL OF OPTOMETRY & PHYSIOLOGICAL OPTICS, Vol. 55, No. 6, pp. 400–406, June 1978; and in "Biofeedback of Accommodation to Reduce Functional Myopia" by Joseph N. Trachtman, Vincent Giambalvo and Jerome Feldman, BIOFEEDBACK AND SELF-REGULATION, Vol. 6, No. 4, 1981. Here functional myopia was defined as being limited to −1.25 diopters, and while improvements in the relatively slight myopic conditions of three experimental subjects were demonstrated, the same were somewhat limited.

In the research reported by T. N. Cornsweet and H. D. Crane, for example, the experimental subjects were established within an experimental environment wherein a dim point was viewed through an artificial pupil and accommodation was measured through an automatic infrared optometer. Feedback pertaining to their state of accommodation was provided through one earpiece of a binaural headphone set while a manually alterable tone was provided through the other earpiece. The experimental subjects were, in effect, told to manually vary the tone in one earpiece and alter their accommodation on an ad lib basis until the response tone fed back matched the tone which had been set. Two experimental emmetropic subjects were utilized and each required three hours of ad lib practice to fully perform the task assigned. However, once voluntary control of accommodation was learned employing auditory tone matching techniques, the voluntary control learned was apparently retained when the feedback technique was changed to employ optical matching techniques. This, however, was purely an experiment pertaining to voluntary control of the ciliary muscle since experimental emmetropic subjects can, by definition, contract and relax their ciliary muscle to achieve proper focus.

In my own experiments, as noted above, the experimental subject's accommodation was again measured by an automatic infrared optometer. The research utilized a sophisticated experimental design (single subject, double reversal, and multiple baseline), and functionally myopic experimental subjects having a refractive error of from −0.25 to −1.25 diopters were employed. The training was conducted in a dark environment and testing was conducted under computer control in such manner that baseline and feedback periods were interleaved according to a single subject, double reversal, multiple baseline technique which allows the experimental subject to act as his own control. More particularly, during each baseline period a green fixation dot placed beyond optical infinity was actuated and the experimental subject was requested to look at the light and depress a response key. This continued for eight seconds and then the fixation light was deenergized and the experimental subject allowed to rest his eyes for four seconds only. White noise was supplied to the headphones during the interval when the fixation dot was illuminated and each minute of baseline measurement by the optometer operating under computer control was made up of five cycles, as outlined above. Baseline periods made up of one minute or more were then followed by training periods randomly chosen of unequal duration of the same makeup as the baseline intervals, i.e., eight seconds of training followed by a four second rest interval.

During training periods, feedback in the form of tone information was provided to the headphones under conditions where the tone produced was directly proportional to the accommodative status of the experimental subject, each 0.125 diopter change in accommodation producing a 50 Hz change in tone. For purposes of providing feedback tone information, the mean of two consecutive optometer scans was calculated by the computer, wherein one scan occurred each 31.6 milliseconds and a tone proportional to the mean calculated was provided to the experimental subject within 134 milliseconds of the onset of the accommodative response. The experiments indicated that a clinically significant 0.5 diopter reduction of myopia could be achieved for myopic experimental subjects in the 0.75 to 1.25 diopter range. This corresponds to a Snellen visual acuity change of from 20/65 to 20/25.

Here, too, the experimental subject was merely instructed to make the tone fed back during training intervals as high as possible. The experimental subject was then left alone and the experimental procedure was automatically conducted by the computer. In the experiments conducted, experimental subject fatigue proved to be a problem due to the fixed number of baseline and feedback periods employed and the fixed number of sessions to which each experimental subject was obligated to experience. This periodically resulted in acute spasm of the ciliary muscle manifesting itself as a burning sensation in the eye of the experimental subject. It was also necessary to dilate each experimental subject's pupils to facilitate the measurements to be taken, and it was found that the delay of 134 milliseconds between the initial accommodative measurement and the delivery of the tone by the computer, due to the calculations employed, was too long. Additionally, the computer was employed to calculate the relationship between diopters and the output of the optometer using a least squares fit, and such calibration was performed for each experimental subject for each experimental training session. Alignment of the experimental subject with the instrument was performed solely by observing the output from the retinal image on an oscilloscope, and this technique also proved to be time consuming.

In the experiments conducted all of the training was performed in a dark room in order to achieve a break in the accommodative convergence reflex and to eliminate as many stimuli to accommodation as possible. Thus, the experiments were performed for the purpose of demonstrating that control of accommodation in functionally myopic experimental subjects could be learned in the absence of all stimuli other than voluntary control. There was no attempt to generalize the voluntary control of accommodation which was mastered to an environment which contained stimuli or to permit the same to be implemented in an environment which also contained blur cues. Finally, in the experiment conducted a Badal lens system, having movable Snellen letters mounted on a track, was employed for purposes of initially calibrating the optometer for each training period and a least squares fit was tested to insure a linear monotonic calibration was achieved.

U.S. Pat. Nos. 4,533,221 and (Ser. No. 829,555), of which the instant application is a continuation-in-part, are directed to methods and apparatus for performing accommodation training under clinical conditions to teach voluntary control of accommodation and reduce various visual acuity problems in a patient. Accommodation has been defined as the process of increasing and decreasing the refractive power of the crystalline lens of the eye. For clear distance viewing, a decrease in refractive power obtained through a relaxatin of the ciliary muscle is required; while for clear near viewing, an increase in refractive power is mandated. Functional myopia, as distinguished from congenital or pathological myopia, has been defined as myopia due to a spasm of the ciliary muscle. Conversely, absolute hyperopia is related to an inability to contract the ciliary muscle to increase the refractive power of the lens. Hence, voluntary control of accommodation in a patient will allow a marked increase in the ability of a patent to decrease or increase the refractive power of the lens of the eye, and hence, markedly reduce any marked myopic or hyperopic condition associated therewith.

In the case of functional myopia, for example, simple acquistion of voluntary control of accommodation in a patient has been found insufficient to enable that patient to correct for a blurred image received unless the ability to extend such voluntary control over accommodation is generalized to a normal environment to enable the patient to voluntarily control accommodation in the presence of blur cues and the accommodative convergence reflex. More particularly, my clinical experience with functionally myopic patients has indicated that a general response to perceiving a blurred image is for the patient to overfocus to factually increase blur. This is readily demonstratable when patients are reading eye charts after undergoing some accommodation training. So long as there is something on the eye chart which can be read, voluntary control will properly operate to enable the patient to relax focus, and hence, read succeeding lines on the eye chart. However, when the chart is changed and difficulty is encountered with the first line of the chart, the patient frequently will cause the entire new slide to be blurred out. Instead, if a new chart is provided with at least one large letter which can be easily read, the patient's progress on the next slide will continue in a normal manner wherein the patient may relax his focus and continue reading succeeding lines on the chart. Thus, once a patient has acquired the skill of voluntarily controlling accommodation in an environment free of all blur cues, this control must be extended or generalized to an environment which contains such blur cues.

Similarly, for voluntary control of accommodation to be useful to a patient in controlling focus, that patient must be able to control accommodation in the presence of the neurological reflex known as the accommodation convergence reflex. This reflex, in effect, controls the movement of the eyes toward and away from each other as a function of the accommodation of the eye. Thus, as accommodation is increased, the accommodation convergence reflex will cause the eyes to turn toward one another; while when focus or accommodation is relaxed, the eyes will assume a more parallel relationship so that at optical infinity, an emmetropic patient will have zero accommodation and zero convergence. Accordingly, for a patient to effectively use voluntary control of accommodation to improve vision, such voluntary control is best learned in an environment free of the accommodation convergence reflex and thereafter must be extended to an environment wherein the accommodation convergence reflex is present so that learned voluntary control of accommodation is operative in the presence of this neurological reflex.

Finally, research has indicated that the accommodation mechanism of the eye is subject to 2,047 possible combinations of stimuli which can also trigger the accommodation mechanism. Hence, for any learned voluntary control of accommodation to be useful to a patient in reducing or curing a visual acuity problem, the voluntary control of accommodation which is acquired must be fully operative in the presence of such stimuli.

While each of the considerations noted above are applicable to myopic patients, corresponding considerations also apply to hyperopic patients. For these reasons, the methods and apparatus for performing accommodation training under clinical conditions for purposes of teaching voluntary control of accommodation as taught herein, initially establish an environment wherein a patient is able to acquire control of accommodation free of all blur cues and stimuli to accommodation and where the accommodation convergence reflex loop is broken. Under these circumstances, it will be appreciated that the patient need only learn to control accommodation through the action of the ciliary muscle through positive inputs to the autonomic nervous system. Under these circumstances, biofeedback is provided for purposes of enabling the patient to gauge which of such inputs are achieving the desired result, as well as the degree of control of accommodation which is being exercised. This is continued until such time as the patient acquires substantial voluntary control over accommodation and can promptly control the state of accommodation or relaxation associated with the ciliary muscles to desired levels.

Once proficiency in controlling accommodation is demonstrated absent blur cues, accommodation stimuli, and absent the accommodation convergence reflex, the training is generalized to provide an environment wherein the voluntary control over accommodation may be exercised in the presence of these factors. This, however, is slowly done under circumstances where blur cues of graduated character are inserted, or alternatively, stimuli to accommodation and the accommodative convergence reflex are gradually provided so that the patient's ability to voluntarily control convergence is retained as the environment is slowly generalized. When the patient is able to maintain voluntary control over convergence in an environment wherein the accommodative convergence loop and stimuli to the accommodation mechanism are fully restored and where blur cues of various character are present, the voluntary control of accommodation which has been learned is fully usable by the patient to reduce various visual acuity problems. While the methods and apparatus for performing accommodation training under clinical conditions as taught herein have obvious application to myopic and hyperopic patients, the same have been also found to be useful in treating presbyopia, anisometropia, nystagmus, and strabismus and eccentric fixation.

BACKGROUND OF THIS CONTINUATION-IN-PART

The infrared optometer employed for performing accommodation training may be optically configured to principally detect retinal reflections from the eye being measured. When this is done image radiation being sensed tends to be somewhat insensitive to eye position since corneal and lenticular reflections may attenuated or eliminated. However, lens distance configurations may be selected which provide a substantial component of corneal reflection at the optometer sensor in which case the accommodation measured as a function of retinal reflection is less pronounced but the optometer is rendered highly sensitive to eye position. Under these circumstances essentially the same instrument may be employed as an eye position monitor and utilized in the treatment and correction through training of strabismus, eccentric fixation, nystagmus and related eye position disorders.

Therefore, it is a principal object of the present invention to provide methods and apparatus for monitoring and training eye position under clinical conditions.

A further object of this invention is to provide methods and apparatus for treating strabismus.

An additional object of this invention is to provide methods and apparatus for treating eccentric fixation.

Another object of this invention is to provide methods and apparatus for treating nystagmus.

A further object of this invention is to provide methods and apparatus for treating muscle controlled eye position disorders.

Various other objects and advantages of the present invention will become clear from the following detailed description of an exemplary embodiment thereof and the novel features will be particularly pointed out in conjunction with the claims appended hereto.

SUMMARY OF THE INVENTION

In accordance with the teachings of the present invention, methods and apparatus for performing accommodation training under clinical conditions are provided wherein an infrared optometer is employed to measure a patient's accommodation and the outputs therefrom are employed to generate tone information and patient information indicative of the state of focus in a rapid manner; a patient is trained at an empirical rate determined by the viewable information until a predetermined proficiency in the voluntary control of accommodation is achieved; thereafter, stimuli to accommodation, the accommodation convergence reflex and blur cue information are selectively introduced to generalize the voluntary control of accommodation achieved to a conventional environment so that the same may serve to reduce various visual acuity problems in a patient being trained.

Further, in accordance with the subject matter added by this continuation-in-part, as separately set forth below, methods and apparatus for monitoring and training eye position under clinical conditions are provided wherein an infrared optometer is employed to measure a patient's corneal and retinal reflection and outputs therefrom are employed to generate tone information and viewable patient information indicative of eye position and the state of focus enabling a patient to be trained until a predetermined proficiency in voluntary control of eye positions is acquired.

BRIEF DESCRIPTION OF THE DRAWINGS

The invention will be more clearly understood by reference to the following detailed description of an exemplary embodiment thereof in conjunction with the accompanying drawings in which.

DETAILED DESCRIPTION

Figure 1:
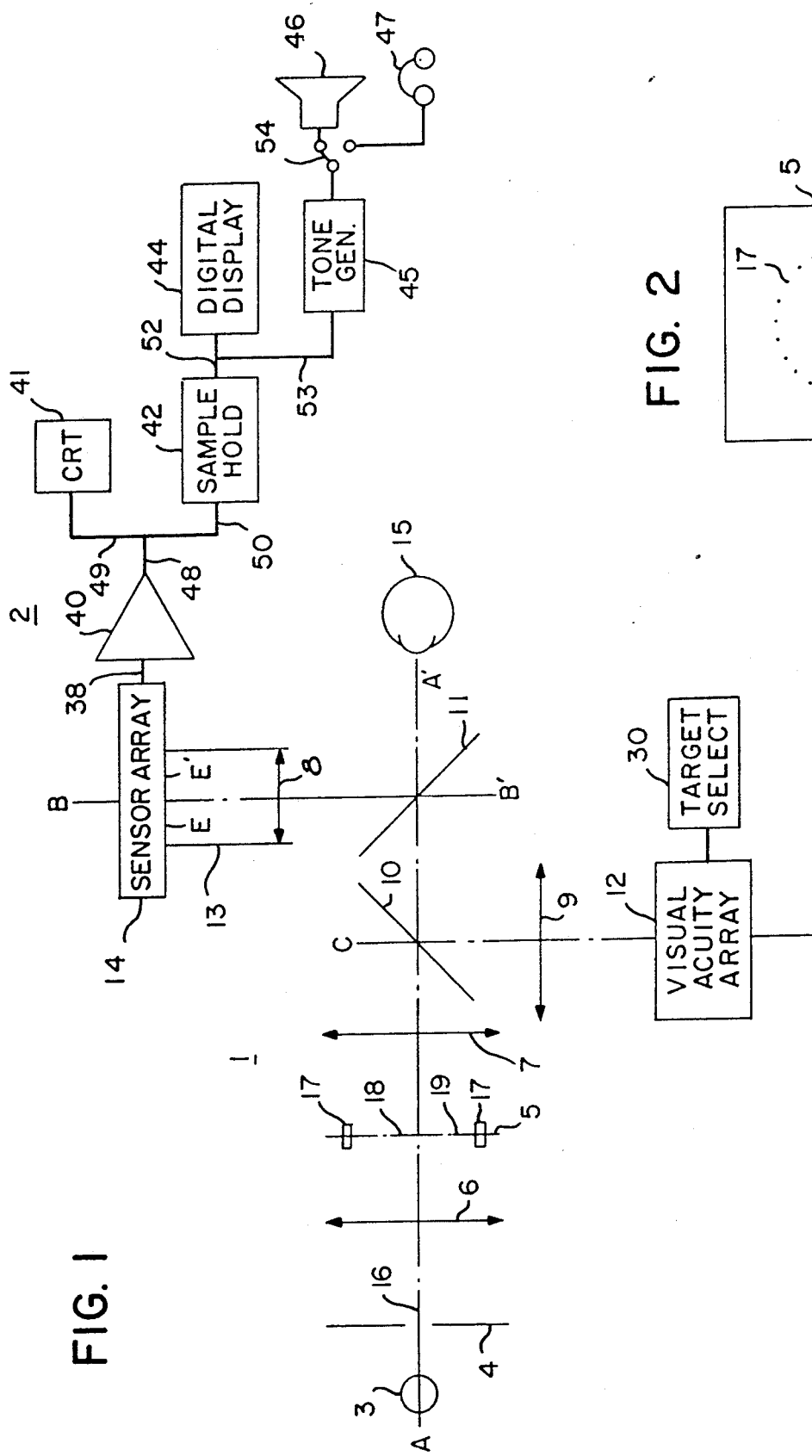
FIG. 1 is a block diagram serving to schematically illustrate a preferred embodiment of a system for performing accommodation training under clinical conditions in accordance with the teachings of the present invention.

Referring now to the drawings, and more particularly to FIG. 1 thereof, there is shown a block diagram serving to schematically illustrate a preferred embodiment of a system for performing accommodation training under clinical conditions in accordance with the teachings of the present invention. The system for performing accommodation training illustrated in FIG. 1 essentially comprises an optometer portion, indicated by the numeral 1, and an electronic portion, indicated by the numeral 2, which is responsive to the output of the optometer for providing biofeedback to the patient being trained, as well as data which is viewable by training personnel for purpose of monitoring the patient's progress and for insuring that the interface established between the patient being trained and the optometer 1 is in proper alignment.

The optometer portion 1 of the system illustrated in FIG. 1 is basically a modification of the optometer described in U.S. Pat. No. 4,162,828 which issued to the instant inventor hereof on July 31, 1979. For this reason, the disclosure of U.S. Pat. No. 4,162,828 is incorporated by reference herein and a detailed description of common structure shall not be set forth in detail unless the same is viewed as necessary for proper understanding of the instant invention. In this regard, it should be noted that while additional structure is added to the optometer disclosed in U.S. Pat. No. 4,162,828 to incorporate certain features of the present invention, and the various optical paths may be somewhat compressed to suit the instant design, the function and modes of operation of the optometer structure per se remains the same. Therefore, those of ordinary skill in the art should make reference to this U.S. patent for additional details concerning the optometer structure which is employed. This particular optometer structure is viewed as highly desirable due to the rapid response time thereof, however, other optometer structure may also be employed.

The optometer structure illustrated in FIG. 1 comprises a source 3, first and second optical slit means 4 and 5, lens means 6-9, first and second beam splitter means 10 and 11, a visual acuity array 12, tube means 13 and a sensor means 14 whose output is supplied to the electronic portion 2 of the system illustrated in FIG. 1.

The infrared source 3 preferably takes the form of a high-powered, infrared light-emitting diode or diode array such as are conventionally available from manufacturers such as Texas Instruments, General Electronic, and TRW. Typically, such a high-intensity LED device or array would be a gallium arsenide device whose output may range from approximately 900 nanometers to 940 nanometers (narrow band rate) and whose output as measured at the cornea of the eye 15 does not exceed 2 watts/$cm^2$. Alternatively, a gallium aluminum arsenide device may be employed as well as a xenon or mercury arc lamp. Whether a single high-intensity infrared LED device or an array is employed is a function of the transmission characteristics of the device. More particularly, whether the narrow band width of a single device is sufficient to fill the first optical slit means 4 or whether a plurality of high-intensity LED devices are required to provide this function. The infrared source 3 would typically be energized in a pulse mode and preferably is pulsed in synchronism with the sensor means 14 which may take the form of a charged coupled array.

The first optical slit means 4 may take any of the conventional forms of optical slit devices well known to those of ordinary skill in the art such as an optical plate having a single slit 16 therein. The single slit 16 is disposed about the optical axis A—A' of the optometer apparatus and is dimensioned such that infrared radiation emanating from the infrared source 3 is restricted to a dimension such that after the same is supplied to the lens means 6, both slits 18 and 19 of the second optical slit means 5 are filled. Thus, since the output from the first optical slit means 4 will form the retinal image, as well as the image on the sensor means 14, the length and width of the optical slit 16 is determined by the available light produced by the infrared source 3 and the differential considerations associated with filling each slit 18 and 19 of the second slit means 5. Typically, the optical slit 16 within the first optical slit means 4 would have a length which may vary between 10 and 20 millimeters and a width which varies from 2 to 4 millimeters.

Reference to U.S. Pat. No. 4,162,828 will readily reveal that the infrared source 3 and the first optical slit means 4 here act to replace the source of illumination 1, the mirror means 2 and the infrared filter means 4 there employed to illuminate the double slit means 9 which here corresponds in function to the second slit means 5. Furthermore, it will be appreciated by those of ordinary skill in the art that should it be desired to replace the infrared high-intensity source 3 and the first slit means 4 with the tungsten source, concave mirror and infrared filter employed in U.S. Pat. No. 4,162,826, the same is readily available. However, reliability considerations associated with the instant design, as well as a restriction in the size of the optical slits associated with the slit means 5, as employed herein, have indicated that use of a high-intensity infrared LED device or array, together with the first slit means 4 is to be preferred. The high-intensity infrared source 3 is displaced in front of the first slit means 4 by a distance which may typically correspond to 10 millimeters along the optical axis A—A' illustrated in FIG. 1, and the first optical slit means 4 is disposed so that the slit 16 therein is centered along the optical axis A—A'. The infrared source 3 and optical slit means 4 may also be replaced by a clamped fiber optic cable serving as a slit source at the location of the first optical slit means 4.

The lens means 6 and 7 may take the conventional form of an achromatic doublet, in the form of condensing lenses of the same type described with respect to lenses 5 and 6 in U.S. Pat. No. 4,162,828. Under these circumstances, it will be apparent to those of ordinary skill in the art that lens means 6 acts to converge radiation passing therethrough from the first slit means 16 so that divergent infrared radiation from the slit means 16 is rendered more convergent or less divergent and supplied to the second slit means 5. For the displacement values given above, the convex lens means 6 may be displaced from the first slit means 4, along the axis A—A', by an exemplary distance of 170 millimeters, and in front of the second slit means 5 by a distance of 77.4 millimeters.

Figure 2:
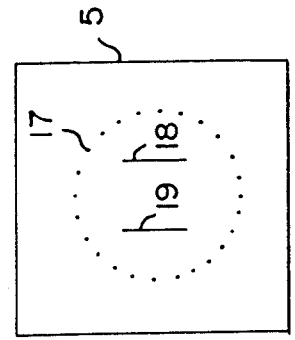
FIG. 2 is a front view of double slit means employed in the embodiment of the invention shown in FIG. 1, this figure showing additional details of the slits employed, as well as an alignment array provided thereon.

The second optical slit means 5, best shown in FIG. 2, may take any of the conventional forms of optical slit devices well known to those of ordinary skill in the art, such as an optical plate having a pair of slits 18 and 19 therein. Slits 18 and 19 are symmetrically disposed about the optical axis A—A' and act, as shall be seen below, as image sources to be focused upon the plane of the pupil of the eye. This occurs as the instant opometer device relies upon the Scheiner principle in that two slits of parallel light in Maxwellian view are projected into the eye. According to the Scheiner principle, when two slits of parallel light are imaged on the pupil, an emmetropic eye will cause a single image of the light source, in this case a single slit, to be focused upon the retina. If the eye is ametropic, a pair of slits will be focused on the retina having a proportional separation therebetween which corresponds to the refraction of the eye. Thus, the displacement between such slits as imaged upon the retina may be employed as a direct measurement of the refraction of the eye, and it is this principle upon which the optometer portion of the instant invention relies.

Because it is desired that the instant invention not require that drugs be employed to dilate a patient's eye, the slit means 18 and 19 are preferably configured so that when the same are imaged upon the plane of the pupil of the eye, such images will be smaller than the diameter of the pupil of the eye of the patient. Absent this result, either drugs will be required for purposes of dilating the pupil, or refraction readings obtained from the sensor means 14 will be reduced by a factor which corresponds to slit radiation which was focused outside of the diameter of the pupil.

Since normal pupil size for patients will average from 3 to 8 millimeters in a dark environment, the slit means 18 and 19 will have a width corresponding to 0.4 millimeters and will be separated from one another by 0.3 millimeter so that the resulting width of the displaced slits about the axis A—A' preferably corresponds to a 1.1 millimeter width which, when projected upon the pupil of the eye 15, is smaller than the lowest portion of the average for pupil sizes as measured in a dark environment. Similarly, the height of each of the slits 18 and 19, as illustrated in FIG. 2, will also correspond to 1.1 millimeters to accommodate the lower portion of the average pupil size within a dark environment. It should be noted that while average pupil sizes of from 3 to 8 millimeters are given in terms of pupil size within a dark environment, and later portions of the training conducted herein occur in a lighted environment, the resulting reduction in pupil size in such lighted environment will not generally remove a patient from the average. Furthermore, readjustment of the electrical portion of the apparatus illustrated in FIG. 1 may be readily achieved, if desired, and, in such subsequent portions of the training, this fact is less significant as relative indication of accommodation is all that is required.

In addition to the optical slits 18 and 19 illustrated in FIG. 2, the second optical slit means 5 has a plurality of LED devices 17 arranged thereon in a ring configuration. The ring of LED devices is selectively energized by switch means or the like, not shown, in a selected manner for purposes of imaging a light ring on the iris for purposes of aligning a patient's eye 15 with the apparatus illustrated. For this reason, the diameter of the ring formed by the plurality of LED devices is approximately 2.88 millimeters and it will be appreciated by those of ordinary skill in the art that when the same is illuminated so that an image thereof is apparent on the iris of the eye 15, infrared radiation from the slits 18 and 19 will automatically be focused on the plane of the pupil of the eye 15. Actual alignment of the eye may be achieved either by displacement of the patient's head or through relative displacement of the instrument.

In this regard, it should be noted that the patient's head is initially steadied with respect to the optical apparatus illustrated in FIG. 1 through the provision of a bite plate or, preferably, a head-and-chin rester which have a base and are displaceable along a horizontal and vertical axis. Once the patient is placed in such relationship, the base is displaced until alignment is achieved, and more particularly, the center of the pupil is in alignment with the axis A—A' shown in FIG. 1. Alternately, the instrument may be selectively displaced with respect to the bite plate or head-and-chin rester. This has previously been done through electronic means, as shall be described in detail below, and was often quite time-consuming. However, in the current invention, a ring formed by the plurality of LED devices 17 is initially switched on when the patient is placed in an operative relationship with the optometer portion of the instant invention. Thereafter, the head-and-chin rester or bite bar is displaced in a vertical and horizontal direction until the ring of light associated with the plurality of LED devices 17 is imaged on the plane of the iris. Once this is done, imaging of light from the slits 18 and 19 on the plane of the pupil is assured. While a ring of LED devices 17 is preferred since the same best accommodates the shape of the iris, other shapes such as ovals, triangles, squares or rectangles may be used as well.

Thus, at this juncture, the plurality of LED devices may be turned off and training either initiated or fine adjustment of alignment may be completed through electronic means to be described below. While a plurality of LED devices 17 has been discussed in association with the selectively illuminated ring configuration of the second optical slit means 5, it will also be appreciated by those of ordinary skill in the art that fiber optics or other types of light rings could be employed to achieve a similar result.

As was discussed above, the location of the second optical slit means 5 is such that infrared radiation which has been converged by the lens means 6 will be imaged on the plane of the pupil of the eye 15. For this reason, the optical slit means 5 may be viewed as displaced in front of the lens means 6 by a distance corresponding to approximately 77.4 millimeters, and the lens means 7 would be positioned in front of the optical slit means 5 by a distance of approximately 85.7 millimeters for the exemplary distances set out above. However, it will be appreciated by those of ordinary skill in the art that wide tolerances in these positions are available, depending upon the focal length associated with the lens means 7.

The lens means 7, as aforesaid, takes the form of one lens of an achromatic doublet in the nature of condensing lenses. Under these circumstances, the first lens 6 of the pair acts to converge infrared radiation being received, while the second lens 7 acts to image the pair of slits 18 and 19, as well as light from the plurality of LED devices 17, if the same are energized, on to the plane of the pupil of the patient's eye 15 and to collimate the infrared radiation from lens means 6. For the exemplary values set forth above, the lens means 6 is displaced from the pupil of the eye 15 along axis A—A' at a distance of 238.1 millimeters so that each of the slits 18 and 19 will be focused on to the plane of the pupil.

Thus, it will be appreciated by those of ordinary skill in the art that the infrared source 3, the first optical slit means 4 and the lens means 6 act to supply more convergent or less divergent infrared radiation to both of the slits 18 and 19 of the second optical slit means 5.

Thereafter, collimated infrared radiation from each of the slits 18 and 19 is imaged by the lens means 7, as a pair of slits, on to the plane of the pupil of the eye 15 and the infrared radiation from lens means 6 is collimated. The center of the pupil will be aligned with the axis A—A'. Accordingly, in this manner, the Scheiner principle is employed to project two slits of parallel light in Maxwellian view into the eye, through the pupil thereof, and image the same on the retina.

In the exemplary embodiment of the invention here being described, the lens means 6 may have a focal length of 63 millimeters and the lens means 7, which may be convex, may have a focal length of 63 millimeters. The pair of slits 18 and 19, as aforesaid, are displaced by approximately 0.3 millimeters, have a width of 0.4 millimeters and a height of approximately 1.1 millimeters to ensure entry of image collimated infrared radiation into the pupil without resort to dilation drugs. Similarly, the ring 17, as illustrated in FIG. 2, may have a diameter of approximately 2.88 millimeters so as to be readily imaged upon the iris.

The optometer apparatus 1 is additionally provided with a side channel by virtue of the visual acuity array 12, the lens means 9 and the first beam splitter means 10. The first beam splitter means 10 may take any of the well-known forms of this conventional class of device. The first beam splitter means 10 acts, in a manner well known to those of ordinary skill in the art, to pass radiation from the lens means 7 along the axis A—A' for imaging upon the plane of the pupil of the eye and retina of the eye 15. Additionally, radiation from the lens means 9 along the axis C—C' is applied along the axis A—A' for purposes of imaging additional radiation, which in this case takes the form of a blur cue image projected on to the retina of the eye 15. Thus, the function of the first beam splitter means 10 is to allow selectively generated target information to be superimposed upon the image radiation of the slits 18 and 19 which are projected on to the pupil and slit 16 which is projected on to the retina.

The lens means 9 may take the form of an achromatic doublet, condensing lens whose focal length should be equal to the distance of the lens to the plane of the pupil of the eye, as measured from the lens means 9 along the axis C—C' to the first beam splitter means 10, and from the beam splitter means 10 along the axis A—A' to the plane of the pupil of the eye. This will insure, as will be readily appreciated by those of ordinary skill in the art, that image radiation applied to the lens means 9 will be projected on to the retina of the eye 15. For purposes of discussion, it may be assumed that the first beam splitter means 10 is disposed 170 millimeters from the plane of the pupil of the eye, as measured along the axis A—A', and hence, the lens means 9 would be displaced along the axis C—C' 40 millimeters from the first beam splitter means 10 or at an optical distance of 80 millimeters.

Since in the exemplary embodiment of the instant invention being discussed herein, four blur cues may be selectively projected on to the retina of the eye, the lens means 9 preferably takes the form of a +4 diopter device to form, in a manner well known to those of ordinary skill in the art, a Badal optometer system. However, it will be readily appreciated that should it be desired to employ only three blur cues, or alternatively, five blur cues, a +3 or +5 diopter lens, respectively, could be used as well.

The radiation applied to the lens means 9 is selectively generated by the visual acuity array 12. The visual acuity array 12 forms the image portion of the Badal optometer established by the visual acuity array 12, the lens means 9 and the optical path established by the beam splitter means 10 on to the retina of the eye 15. More particularly, since the image distance between the lens means 9 and the principal plane of the eye 15 is 250 millimeters and a 4 diopter lens is employed for purposes of projecting radiation from the visual acuity array 12 on to the retina of the eye 15, a target located at 62.5 millimeters behind the lens means 9 will require 3 diopters of focusing power to be clearly seen by a patient. Similarly, a target located at 125 millimeters behind the lens means 9 will require 2 diopters of focusing power to be clearly seen while a target located at 187.5 millimeters behind the lens means 9 will require 1 diopter of focusing power by the patient. In like manner, an object located at 250 millimeters behind the lens means 9 will require 0 diopters of focusing power in a patient.

Therefore, if it is assumed that the patient is nearsighted, the myopic nature of the eye 15 may well be able to clearly see a target focused on the retina of the eye which requires 3 or possibly 2 diopters of focusing power. However, objects requiring 1 diopter or 0 diopters of focusing power will require more relaxation of the ciliary muscle than initially can be brought to bear by a patient. Thus, the selective application of images focused on the retina of the eye by the visual acuity array 12 which require 3, 2, 1 or 0 diopters of focusing power will, in fact, superimpose blur cues on the slit radiation also applied to the eye. Accordingly, in subsequent cycles of training, voluntary control of accommodation learned in a dark environment where no blur cues or stimuli to the accommodation convergence reflex are present can be extended to an environment which does include blur cues requiring increasing relaxation of the ciliary muscle.

Figure 3:
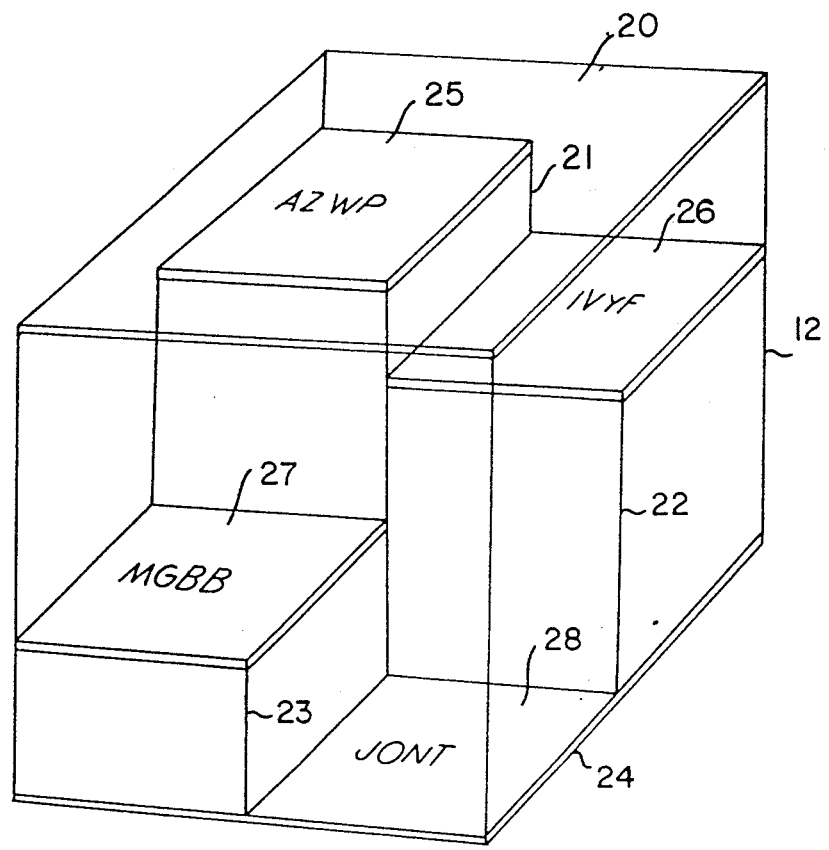
FIG. 3 shows a detailed view of an embodiment of a visual acuity array employed in the embodiment of the invention shown in FIG. 1.

The structure of the visual acuity array 12 could take the form of a target which is displaceable on a track so that the same may be made to assume displacements of 62.5 millimeters, 125 millimeters, 187.5 millimeters and 250 millimeters for the selective projecting of blur cue information on to the retina of the eye; however, the structure illustrated in FIG. 3 is preferred. The reader's attention is directed to FIG. 3 which illustrates a detailed view of an exemplary embodiment of a visual acuity array which may be employed in the embodiment of the invention shown in FIG. 1.

The visual acuity array 12, illustrated in FIG. 3, comprises an optics box having a clear cover 20 made of glass or plastic within which resides four columns 21-24 of differing heights. Each column has a top portion 25-28 having reduced Snellen characters thereon, and the relationship between each of the top portions 25-28 and the lens means 9 is such that the fixed displacements are established. Thus, the top portion 25 is displaced from the lens means 9 by a distance of 62.5 millimeters, the top portion 26 is displaced from the lens means 9 by a distance corresponding to 125 millimeters, the top portion 27 is displaced from the lens means 9 by a distance corresponding to 187.5 millimeters, and the top portion 28 is displaced from the lens means 9 by a distance of 250 millimeters.

Each of the top portions 25-28 of the columns 21-24 may be formed of opaque material with the reduced Snellen characters being disposed upon transparent material which preferably has an overall dark cast. Within each column is an LED device (not shown)

which may be selectively illuminated by a switch means present in the target select circuit 30 illustrated in FIG. 1 or the reduced Snellen letters may take the form of an LCD. Thus, whenever the target select circuit 30 illustrated in FIG. 1 is enabled by the actuation of an appropriate switch assigned to each of the columns 21-24, one of the targets within the columns 21-24 will be illuminated. This will cause image radiation associated with the reduced Snellen characters thereon to be projected on to an appropriate area of the retina of the eye.

In this manner, whenever an operator has determined that training has continued to a point at which the voluntary accommodation which has been learned should be practiced in the presence of blur cue information, an appropriate one of the reduced Snellen character information associated with the columns 21-24 may be selectively projected on to the retina of the eye, depending on the appropriate selection of switches at the target select means 30 illustrated in FIG. 1. Should the patient be myopic, obviously the operator would start with column 21 and increase blur information as training continued toward column 24. For hyperopic patients, the reverse procedure would be employed.

While not illustrated in FIG. 1, the room in which the training system illustrated in FIG. 1 is located should be equipped with a lighting system having a rheostat or other form of dimmer control. This is desirable so that the trainer may, during succeeding portions of the training process, selectively and periodically increase the ambient light level in the room to restore the patient's accommodation convergence reflex and various stimuli to accommodation as training continues. Thus, while the patient does not discern the image slit radiation imaged at the plane of the pupil of the eye, due to the nature of the infrared radiation employed at various intervals during the course of the training, to be discussed in greater detail below, blur cue information which is discernable to the patient will be projected on to the retina of the eye so as to appear in a portion of what the patient perceives. Additionally, in an independent manner, the ambient light level of the training environment will be brought up to restore the accommodation convergence reflex and various stimuli to accommodation as the training proceeds.

Returning now to a discussion of FIG. 1, it will be appreciated by those of ordinary skill in the art that the two slits of infrared light focused on the plane of the pupil of the eye 15, in Maxwellian view, will allow the single slit source means 4 to be imaged back on to the retina in a manner well known to those of ordinary skill in the art. If the eye 15 of the patient is emmetropic, and also has no accommodation, a single slit of light will be formed on the retina in accordance with Scheiner's principle. However, if the eye 15 is ametropic, a pair of slits will be formed on the retina having a proportional separation therebetween which corresponds to the refractive error in the eye. Thus, as is well known to those of ordinary skill in the art, for a myopic condition an image of a single slit will be focused in front of the retina, and hence, the retinal image corresponding to a doubled slit will be formed, depending upon the degree of the myopic condition. Conversely, in a hyperopic condition, a single image of a slit would form behind the retina, and for this reason a doubled slit will be formed on the retina. In each case of a doubled slit image on the retina, the displacement therebetween corresponds to a measure of the refraction of the eye which can be directly translated into the appropriate prescription necessary for correction, it being appreciated that the instant measurement is occurring only along one meridian. Thus, it will be appreciated by those of ordinary skill in the art that, in response to the imaging of a pair of slits on the plane of the pupil of the eye 15 through which a single slit source of parallel radiation is projected, a retinal image is formed which will correspond to either a single slit if the eye is emmetropic and has no accommodation, or a doubled slit for an eye exhibiting a change, either an increase or a decrease, in refraction associated with an ametropic condition.

Whatever retinal image is formed will be reflected back to the beam splitter means 11. The beam splitter means 11 may take any of the conventional forms of this common class of device and acts in the well-known manner to pass radiation from the lens means 7 therethrough for imaging at the pupil and retina of the eye 15 while image radiation reflected back from the eye is communicated by the beam splitter means 11 toward the lens means 8. The beam splitter means 11 is displaced from the plane of the pupil of the eye by a distance which may typically correspond to approximately 132 millimeters as measured along the central axis A—A' of the device, and acts in the well-known manner to direct radiation corresponding to that reflected from the image in the eye towards the lens means 8. The lens means 8 may also take the form of an achromatic doublet, condensing lens which acts to focus the retinal image upon the sensor array 14. The lens means 8 should be at an appropriate distance to eliminate corneal and lenticular reflections and have a focal length, for example, which may typically be 88 millimeters. The lens means 8 may be disposed above the axis A—A' by a distance of approximately 44 millimeters in such manner that its central axis corresponds to the point of intersection with the axis A—A' and the beam splitter means 11. Thus, it will be appreciated by those of ordinary skill in the art that the retinal image is communicated from the beam splitter means 11 through the tube means 13 and imaged upon the sensor means 14.

The tube means 13 may take the form of a cylindrical tube made of any opaque, convenient material and functions in the well-known manner to prevent spurious light from being introduced into retinal image radiation being conveyed from the lens means 8 to the sensor means 12. The diameter of the tube means 13 is such that it preferably accommodates a mounting of the lens means 8 therein and it is of a length which is deliberately selected so that the same exceeds the focal length of the lens means 8. This effects a distal mounting of the sensor array 14 in order that the conjugate of the retinal image is formed thereon. In this manner, a discrete range of retinal images are representative of a hyperopic or farsighted condition, while a second discrete range of images are representative of a myopic or nearsighted condition. Thus, while the function of the tube means 13 is principally to isolate retinal image radiation being conveyed through the lens means 8 from ambient radiation to enhance the sensitivity of the sensor means 14, and hence, improve the signal-to-noise ratio of the output thereof, the length of the tube means 13 and the focal length of the lens means 8 also determine the nature of the image radiation imposed upon the sensor means 14.

For example, if the length of the tube means 13 were selected to be identical to the focal length of the lens means 8, the retinal image would be formed directly at the surface of the sensor means in such a manner as to directly correspond to the retina image formed at the eye 15. This, however, would not provide an indication, in the case of an ametropic eye, as to whether or not a myopic or hyperopic condition were being measured. For instance, in the case of an emmetropic eye exhibiting no accommodation, a single image of the slit would be formed on the retina as aforesaid, and accordingly, a single image of the slit retinal image would be formed at the sensor means at the axis B—B'. However, for an ametropic condition wherein two slits form the retinal image, the distance between the slits would be proportional to the correction required regardless of whether or not a myopic or hyperopic condition is present. Thus, were the length of the tube means 13 equal to the focal length of the lens means 8, while the distance between the pair of slits formed would be a measure of the refraction of the eye, no clear indication of a myopic or hyperopic condition would be present.

However, it will be apparent that for a myopic condition, divergent radiation will form the retinal image while, conversely, for a hyperopic condition less divergent radiation forms the retinal image. This means that if the length of the tube means 13 is made to be less than or greater than the focal length of the lens means 8, the characteristic divergent or convergent condition of the radiation associated with an image for a myopic or hyperopic condition, respectively, may be employed to distinguish the condition. Thus, it will be appreciated by those of ordinary skill in the art that in the case of the length of the tube means 13 being less than the focal length of the lens means 8, the divergent nature of the pair of slits formed on the retina of the eye due to a myopic condition will cause images associated therewith to fall within a certain range indicated as E—E' at the surface of the sensor means 14. Conversely, pairs of slits associated with a hyperopic condition will cause image radiation associated with the pair of slits formed to fall outside of the range E—E' at the surface of the sensor means 14.

Here the length of the tube means 13 has been selected to be greater than the focal length of the lens means 8 so that a conjugate image will be formed at the surface of the sensor means 14. Under these conditions, the image radiation associated with the pair of slits 18 and 19 from a hyperopic condition will fall within the range E—E', while image radiation associated with a pair of slits from a myopic condition will fall external to the range annotated E—E' at the surface of the sensor means 14.

Figure 4:
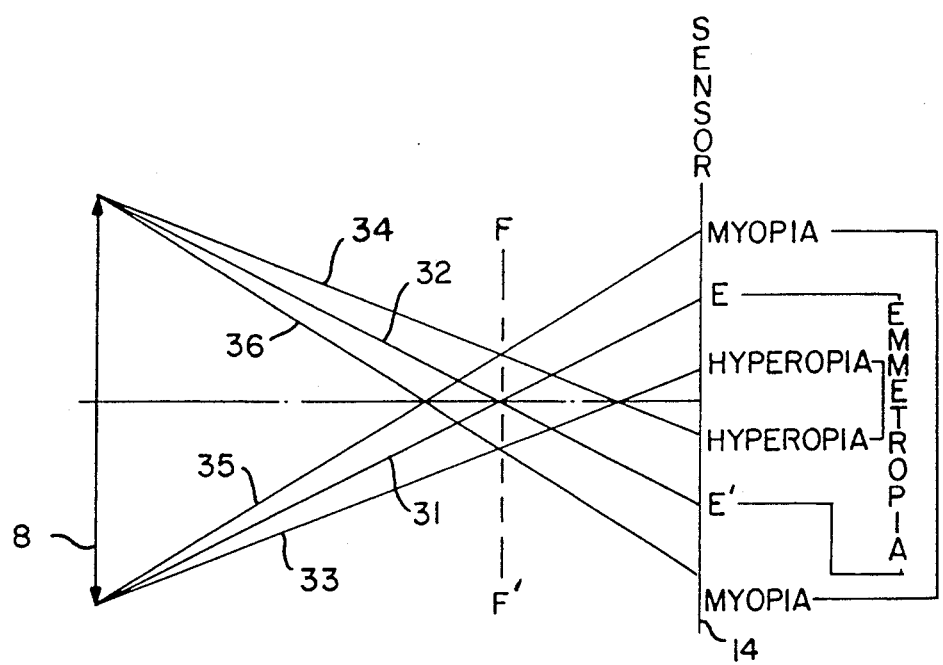
FIG. 4 illustrates the manner in which myopic, emmetropic and hyperopic conditions of accommodation are sensed in the embodiment of the invention shown in FIG. 1.

This can best be seen by reference to FIG. 4 which illustrates the manner in which myopic, emmetropic and hyperopic conditions of accommodation are imaged upon the surface of the sensor array 14 and sensed in the embodiment of the invention illustrated in FIG. 1. In FIG. 4 the lens means 8 and the sensor means 14 are shown, the sensor means 14 being distal to the lens means 8 in that the mounting distance exceeds the focal length of the lens means 8.

In FIG. 4, the actual focal length of the lens means 8 is indicated by the dashed line F—F'. As will be seen upon an inspection of FIG. 4, radiation corresponding to image information from an emmetropic eye is indicated by the rays annotated 31 and 32, and it will be seen that they converge to a single slit at the axis F—F' corresponding to the focal length of the lens means 8. However, since the sensor means 14 is mounted distal to the lens means 8 due to the length of the tube means 13, radiation in the form of a pair of slits corresponding to that information imaged at the pupil of the eye will be imaged upon the face of the sensor means 14 at the locations annotated E—E'. Due to the converging nature of image radiation associated with a hyperopic eye, image radiation from the retina, as supplied from the beam splitter means 11 and supplied to the lens means 8, will refract from the lens means 8 as indicated by the rays annotated 33 and 34 to form an image behind the axis F—F'. This radiation is imaged on the face of the sensor means 14 at the locations indicated within the ambit E—E' associated with image radiation from an emmetropic eye. Conversely, image radiation from the retinal image of a myopic eye will be refracted by the lens means 8, as indicated by the rays annotated 35 and 36, and be imaged upon the sensor means 14 at the locations annotated myopia. These locations will fall outside of the locations on the sensor annotated E—E' associated with an emmetropic eye. Thus, it will be appreciated by those of ordinary skill in the art that through a distal mounting of the sensor means 14, not only is the refraction of the eye indicated by the displacement of image information on a face of the sensor means 14, but also the location of such image information within or without the sensor locations annotated E—E' will also act to define the nature of the condition.

The actual range E—E' will vary with respect to the relationship between the length of the tube means 13 and the focal length of the lens means 8. In a preferred embodiment of the instant invention, the length of the tube means 13 was selected to be 105 millimeters when the focal length of the lens means 8 was 88 millimeters. It should be noted that the conjugate image formed by a tube means 13 having a length which exceeds the focal length of the lens means 8 is preferred, since optical packaging is facilitated thereby and sensor contamination from radiation being focused upon the pupil is more readily avoided. However, those of ordinary skill in the art will recognize that the utilization of a tube means 13 having a shorter or equal length to the focal length of the lens means 8 could be employed as well.

The sensor means 14 preferably takes the form of a linear charged coupled device such as a Reticon RL512C photodiode array connected with a Reticon RC400 clock and counter circuit. These devices act in a manner well known to those of ordinary skill in the art to receive image radiation corresponding to a gradient and to provide a plurality of voltage outputs at a preselected scanning rate corresponding to the intensity of the gradient received along the sensor means 14. The exemplary sensor means 14, noted above, comprises 512 silicon photodiodes mounted on two mil centers. Each photodiode is provided with an associated storage capacitor on which to integrate photocurrent and a multiplex switch in the form of an MOS transistor for periodic readout via an integrated shift register scanning circuit.

As such, the sensor means 14 acts as a light scanner for light intensity along the narrow area defined. While operation of such a light scanner in a charged coupled or charged storage mode is preferred due to the ready availability of commercial devices of this type, it will be appreciated by those of ordinary skill in the art that other sensor means could be employed as well. However, the sensor geometry should be such that a large number of discrete outputs may be obtained along the length thereof to produce an output voltage corresponding to a point-to-point representation of the light intensity imposed thereon.

The overall length of the sensor means 14, in the form of a charged coupled array, is approximately a one-half inch linear array. In the exemplary embodiment of the instant invention, the same is arranged to scan once every 30 milliseconds and produce an output of approximately 0 to 4 volts d.c. for each of the 512 photodiodes present. The clocking rate supplied by the Reticon Model RC400 mother board and a Model RC402 driver amplifier board may also be employed to generate the clock for purposes of the infrared source 3 which may be operated in a pulse mode, as aforesaid.

As thus constituted, it will be appreciated by those of ordinary skill in the art that the retinal image focused upon the sensor means 14 will be transduced by each of the 512 diodes therein, scanning at a rate corresponding to one scan for each 30 milliseconds, so that an output is produced from each photodiode which varies in accordance with the intensity of the radiation imposed thereon. Accordingly, the output of the sensor means 14 produced on the conductor 38 will take the form of a Gaussian energy distribution of the retinal image which may be directly correlated in terms of the refraction of the eye measured.

The use of the linear charged coupled array described above is highly advantageous in that the same provides a direct reading of the refraction of the eye. Further, the representative Gaussian energy distribution obtained of the retinal image is highly precise since the signal-to-noise ratio of the device is very substantial. For an emmetropic eye, the output of the sensor means, as viewed on a scope, will take the form of a bell curve established between the locations indicated as E—E' in FIG. 4. For a myopic eye, this curve is somewhat flattened and spread out between the locations indicated for myopia; while for a hyperopic eye, the curve will be peaked and more narrow in format. Each configuration is readily discernable on a scope.

While a charge coupled device having 512 photodiodes has been discussed, it should be noted that a smaller or larger array such as one containing 128 or 1024 linear elements, respectively, could be employed as well. The size of the array is dependent upon the width of the slits 18 and 19 which are utilized and the distance of the sensor means 14 from the lens means 8. The limiting factor is the resolution which is preferably maintained at approximately 0.01 diopter for an exemplary 20 diopter range extending from −5 diopters of hyperopia to +15 diopters of myopia. The sensitivity of the sensor is determined by the amount of light reaching the sensor from the focused retinal reflection.

Should the pupil size of a patient be such that slit radiation cannot be fully focused thereon, some reduction in the intensity of the output will occur, and hence, an adjustment therefor is required. However, as the same will result in a linear deviation, adjustment may be simply achieved through calibration by way of adding an appropriate constant.

Furthermore, while a scanning rate for the sensor array 14 of 30 milliseconds has been discussed, it will also be appreciated by those of ordinary skill in the art that this is also subject to variation. However, here it is important to note that it has been determined that for purposes of training, it is highly important that a patient be provided with prompt information as to the state of any accommodation change and that miniscule changes in accommodation be indicated. Therefore, a highly sensitive optometer device together with a relatively high sensing rate is of substantial importance. Thus, in the case of the embodiment of the invention being discussed herein, the focus of the eye is measured at least 33 times a second and the optometer employed displays a sensitivity of 0.01 diopter within the range of interest.

Similarly, while a linear array has here been discussed, it will be appreciated by those of ordinary skill in the art that use of a two-dimensional array or matrix sensor coupled with an imaging of a circular or square image on the retina, will yield measurements indicating total refraction of the eye. This would allow for measurement and training for conditions which include dynamic astigmatism.

The output of the sensor array 14 is supplied through the conductor 38 to the electrical portion 2 of the training system illustrated in FIG. 1. The electrical portion 2 of the training system illustrated in FIG. 1 comprises amplifier means 40, a cathode ray tube 41, a sample-and-hold network 42, a digital display 44, tone generator means 45 and acoustical output means 46 and 47. The amplifier means 40 may take any of the well-known forms of this conventional class of device which acts to increase the gain of the output of the sensor array means 14 supplied thereto on conductor 38 to a level of 0 to 5 volts d.c. at the output thereof on conductor 48. Thus, for instance, the amplifier means may comprise a plurality of operational amplifiers such as a Model 741 amplifier as available from Texas Instruments. Alternatively, any other well-known form of this conventional class of device may be employed.

The output of the amplifier means 40, as provided on the output conductor 48, is connected through a first conductor 49 to the input of the cathode ray tube display 41 and through a second conductor 50 to the input of the sample-and-hold network 42. The CRT display 41 may take any of the conventional forms of this well-known class of display device readily available to those of ordinary skill in the art. For instance, in actual models of the instant invention which were built and tested, a conventional oscilloscope was employed for purposes of the CRT display 41. The function of the CRT display 41 is to provide a display of the distribution output by the sensor array 14 in response to its sensing of the retina image.

Furthermore, the CRT display 41 acts to enable fine tuning of the alignment of the patient's eye 15 when the plurality of LED devices are employed for purposes of initial alignment or as an alternate alignment device. Thus, utilization of an oscilloscope for the CRT display 41 is highly advantageous as the selective sweep rate thereof can be made to precisely accommodate the output of the sensor array 14. Further, since the same may be readily calibrated in terms of volts, the magnitude of the peaks obtained for each Gaussian distribution read from the sensor array 14 may be readily ascertained. Those of ordinary skill in the art will appreciate that use of the CRT display 41 for alignment purposes will occur by establishing a patient's eye 15 in relation to the optometer portion of the system illustrated in FIG. 1. Thereafter, the vertical and horizontal position of the eye is adjusted until a well-defined peak is displayed whose magnitude is indicative that alignment has been achieved. Thereafter, the CRT display 41 will serve as an observation instrument for the trainer so that the manner in which the patient is exercising voluntary control of accommodation may be determined.

The sample-and-hold network 42 may take any of the well-known forms of this conventional class of device which acts to receive the amplified output of the sensor array 14 and maintain the peak value thereof until such time as a subsequent output occurs. This is necessary, as will be readily appreciated, since it is desired to provide a patient being trained with continuous tone information representative of the state of his accommodation. Therefore, to avoid a condition where the tone information fed back to the patient is intermittent in nature, varying as a function of the scanning rate of the sensor array 14, the sample-and-hold network 42 is employed to sample and maintain a previous voltage level corresponding to the amplified output of the sensor array 14 until such time as a succeeding sample is obtained. For purposes of the instant discussion, the sample-and-hold network 42 may be viewed as taking the form of an integrator formed by a serially connected resistor and a capacitor connected between the resistor and ground. Under these circumstances, the RC time constant employed would be based upon the scanning rate of the sensor array 14. If appropriate, the output of the integrator could be connected to another amplifier stage, again taking the form of a Model 741 op amp or the like, to avoid signal degradation. The output of the sample-and-hold network 42 is supplied through the conductors 52 and 53 to the input of the digital display 44 and the tone generator means 45.

The digital display 44 may take the conventional form of a digital volt meter or digital panel meter which is calibrated to display the diopters. More particularly, it has been found that there is a linear relationship with respect to the amplified output voltage of the sensor array means 14 and diopters. Therefore, a digital volt meter which is provided with a zero adjust and a slope adjustment for the meter can be readily calibrated to read diopters directly. In this regard, it should be noted that the zero adjust associated with the meter is sufficient to calibrate the same to read diopters for normal cases wherein the patient's pupil is wider than the slit information which is focused thereon. Once such adjustment is made, it is sufficient for all patients which are accommodated within this category. The slope adjustment is only necessary for patients whose pupil size is somewhat smaller than the slit radiation projected. Under these circumstances, correction in the slope is required. It is preferred that the digital display have numerics which are at least one-half inch high and such display include at least four digits with a + and − indicator. Additionally, the digital display should have a jack for purposes of providing output information to a chart recorder or the like so that a real time historical record of the patient's progress may be made. Additionally, a business or other form of small scale computer may be employed for purposes of patient record maintenance and an analog meter may be employed in place of a digital meter.

The tone generator means 45 may take any of the conventional forms of this well-known class of device which acts to transform the voltage supplied thereto on conductor 53 into frequency as a function of the magnitude of such input voltage. Thus, a voltage-controlled oscillator, or complex noise generator chip, may be employed with or without added amplification. In an exemplary embodiment of the instant invention, a BK Precision 3010 function generator was employed with the 1K scale set to 0.1-10 Hz. In this regard, it should be noted that clinical testing has indicated that training results are improved if the frequency of the output tones are maintained within a range of 100 to 10,000 Hz. However, it is preferred to have several subsidiary ranges within this broad frequency range which may be selectively chosen to accommodate the preferences and sensitivities of a given patient. It should also be noted that human hearing is most sensitive to tones in the range of 700 to 2,000 Hz.

The output of the tone generator means 45 is connected through a switch means 54 to the acoustical output means 46 and 47. The acoustical output means 46, as indicated, takes the form of a conventional speaker while the acoustical output means 47 takes the form of acoustic headphones. The switch means 54 is conventional and acts, as will be readily appreciated by those of ordinary skill in the art, to select between the speaker and headphones to accommodate the preferences of the patient. The trainer monitors the patient's progress as a function of what is displayed by the digital display 44.

In operation of the embodiment of the invention illustrated in FIG. 1, the device is energized from a power source, not shown. The patient is placed in an operative relationship to the optometer so that one of the patient's eyes is positioned in the manner indicated in FIG. 1. In this regard, it should be noted that for training purposes for a myopic or hyperopic condition, the eye employed generally does not matter so long as the condition occurs in both eyes even though the same is present to an unequal degree. This occurs since the voluntary control over accommodation which is learned appears to function in an equal manner with respect to both eyes. However, in cases of myopic anisometropia, it is recommended to train the more myopic eye first.

The patient is placed in an operative relationship to the optometer apparatus through the use, as aforesaid, of a bite plate or head-and-chin rester, not shown. These devices are displaceable along a horizontal and vertical axis so that adjustment for alignment of the pupil of the eye 15 with the axis A—A' can readily be implemented. Alternatively, the optometer optics may be rendered displaceable with respect to the patient. At this juncture, the plurality of LED devices 17, arranged in a ring as shown in FIG. 2, are energized and the patient's head is horizontally and vertically displaced until the ring image associated with the plurality of LED devices 17 is imaged upon the iris in a manner so as to be concentric about the pupil. Once this is done, alignment is achieved and the plurality of LEDs 17 are deenergized through switch means, not illustrated. In this regard, it should also be appreciated that alignment may be checked by viewing the display on the CRT display 41, to be described hereinafter, and any fine adjustment with respect to the position of the patient's eye 15 may be further implemented until such time as an appropriate peak is displayed on the CRT display 41.

Since the infrared source 3, the sensor array 14 and the electronics portion of the circuit indicated at 2 in FIG. 1 are enabled, the patient may perceive a dull red glow associated with the infrared source 3 and hear tone information through either the speaker 46 or the headphones 47 indicative of the current state of accommodation. The dull red glow may be present since the infrared source 3 may pass some visible spectrum through to the patient. However, no real image radiation will be received by the patient and the patient will be wholly unaware of the slit information 18 and 19 focused upon the pupil. It should also be noted that the ambient illumination in the room should be controlled in such manner that training initially occurs within a dark environment so that both the accommodation convergence reflex and all stimuli to accommodation are removed. Under these initial conditions, the accommodation of the eye 15 will be a result of voluntary control being exercised by the patient. Once voluntary control is established and can be properly manipulated by the patient, the ambient light level of the room is slowly brought up and blur cue information is periodically provided so that the voluntary control learned can be generalized to a normal environment. However, at the outset, all of the complex factors which normally influence the accommodation of the eye are removed so that the patient may concentrate on the development of voluntary control.

The infrared source 3 may be operated in a pulse mode, as aforesaid, and the clocking rate thereof may conveniently be at the same 30 millisecond rate associated with the sensor array means 14. Radiant infrared energy from the infrared source 3 is thus applied to the first optical slit means 4 in such manner, as aforesaid, so that the slit 16 therein is filled. Under these circumstances, as will be readily appreciated by those of ordinary skill in the art, divergent infrared radiation from the slit 16 is applied to the lens means 6 where the same is made more convergent or less divergent and supplied to the second optical slit means 5 containing symmetrically disposed slits 18 and 19. The radiation from the slits 18 and 19 within the optical slit means 5 is then applied to the lens means 7 where the same is focused through the first and second beam splitter means 10 and 11 and imaged on the plane of the pupil of the eye 15 and the radiation from lens means 6 is collimated by lens means 7. The slits 18 and 19 are specially configured, as aforesaid, so that their radiation is sized to fit within the pupil. The slit information focused on the pupil of the eye is not discernible by the patient and the intensity of the infrared slit information focused on the plane of the pupil was approximately 4 microwatts per centimeter squared in the embodiments of the invention which were built and tested.

The radiation from the pair of slits 18 and 19 as imaged on the plane of the pupil of the eye 15 will form an image of the first optical slit means 4 on the retina, which image will be a function of the refraction of the eye 15. Thus, in accordance with Scheiner's principle, if the eye is emmetropic and displays no accommodation, a single slit will be formed on the retina at the axis A—A', while if an ametropic eye is present, a pair of slits will be formed on the retina wherein the separation between the slits formed is proportional to the correction required and represents the current state of accommodation of the eye.

Radiation corresponding to the retinal image formed is applied by the beam splitter means 11 to the lens means 8 and through the tube means 13 to the surface of the sensor array means 14. Due to the distal mounting of the sensor array 14 at the end of a tube means 13, a conjugate of the retinal image is formed on the surface of the sensor array means 14 in the manner illustrated in FIG. 4. Therefore, while the distal displacement of the sensor array means 14 does not effect the image location of slit information associated with an ametropic eye with respect to the location of slit information from an emmetropic condition, the convergent and divergent radiation associated with a retina image consisting of a pair of slits is readily discernible. Thus, converging radiation associated with a hyperopic condition will be imposed within the range indicated as E—E', while divergent retina image information associated with a myopic condition will fall outside of the range E—E'.

The image radiation placed on the surface of the sensor array means 14 by the lens means 8 will cause each of the 512 photodiodes therein to output photocurrent which is proportional to the light intensity or irradiance received. A charge proportional thereto will thus be stored upon the capacitor associated with each photodiode. Every 30 milliseconds each of the capacitors is read out so that, in effect, a series of 512 voltage pulses which range from 0 to 4 volts d.c. will be placed on the conductor 38 to form a Gaussian energy distribution representing accommodation each 30 millisecond interval. Thus, the output of the sensor means 14 corresponds to a scan of the Gaussian energy distribution of the retinal image applied to the sensor array means 14 wherein a maximum voltage condition corresponds to the central location of slit image information, and the spatial distribution thereof with respect to the axis B—B' corresponds to the accommodation or refraction of the eye, as well as the correction required.

The output of the sensor array means 14 is applied through the conductor 38 to the amplifier means 40 which applies a gain thereto such that the resulting output will vary from 0 to 5 volts d.c. This output is then applied through the conductors 48 and 49 to the CRT display 41. Assuming the CRT display 41 is set to an appropriate sweep, the Gaussian distribution output by the sensor array 14 will be displayed thereon in such manner that the peak value of the voltage distribution and the width thereof will readily indicate the refraction and accommodation of the patient's eye. The width of the distribution will readily indicate the condition which is present.

For instance, a review of the conditions depicted in FIG. 4 will readily demonstrate that for a hyperopic condition, a narrow curve having a maximum voltage peak will be displayed. For an emmetropic condition, a wider curve having a smaller voltage peak will be displayed. Similarly, for a myopic condition, a wide curve having even a smaller voltage peak will be displayed. Furthermore, those of ordinary skill in the art will recognize that the differential in the peak of voltage displayed on either side of the emmetropic value will readily indicate the degree of accommodation present, while the width of the condition's deviation from the width associated with an emmetropic eye will establish the nature of the condition involved.

As far as alignment of the patient's pupil with the axis A—A' is concerned, it will be appreciated that when the patient is properly aligned, a curve having a well-defined peak of some value corresponding to the Gaussian energy distribution of the sensor array 14 should be displayed on the CRT display 41. Thus, this approach too serves as a valid form of aligning the patient with the instrument. However, it is preferable that the patient be initially aligned with the instrument employing the plurality of LED devices 17, and thereafter, the CRT be inspected to insure a maximum peak condition for the eye in question.

The output of the amplifier means is also supplied through the conductors 48 and 50 to the sample-and-hold circuit 42. The sample-and-hold circuit 42 acts in the conventional manner to sample a voltage being applied thereto and to hold the same until a new voltage is presented. In the case of the instant invention, the time constant associated with the sample-and-hold circuit 42 will be appropriately related to the scanning rate of the sensor array means 14 such that the sample-and-hold circuit 42 will assume an output voltage condition corresponding to the peak value of the output on conductor 38 for each scan. This value is retained until a voltage peak associated with a new scan rate is presented.

This is done, as will now be appreciated by those of ordinary skill in the art, to insure that the biofeedback presented to a patient being trained is not intermittent in character and that the only changes in tone relate solely to changes in the accommodation of the eye 15. This feature is quite important as it should be appreciated that the patient will be attempting to vary the accommodation of the eye and is relying upon the acoustic biofeedback provided to ascertain whether this objective is being achieved.

Typically in the case of a myopic patient, the patient will be attempting to reduce the accommodation of the eye from that associated with a myopic condition to that associated with an emmetropic condition. Thus, a tone change which corresponds thereto is sought. It is therefore of paramount importance that the acoustic information provided, which is obtained from the output of the sample-and-hold means 42, reflect only changes in accommodation and not intervals between measurement. Furthermore, it is also highly important that the patient be provided with information pertaining to any change in accommodation in an almost immediate manner and it is for this reason that accommodation is measured 33 times a second.

The output of the sample-and-hold circuit 42 is supplied through the conductor 52 to the digital display 44. The digital display means 44 may take the form of a digital panel meter or volt meter which is calibrated to display diopters. The characters in the digital display should be approximately one-half inch high and a four digit display having a + and − indicator is preferred. Since it has been found that diopters have a linear relationship to the output voltage of the sensor array means 14, it will be appreciated that calibration of the digital display means 44 in terms of diopters is accomplished for all patients having a pupil size which accommodates the slit information provided by establishing a zero value on the display for an emmetropic condition having zero accommodation. Thereafter, a myopic reading will be directly indicated in diopters at the digital display 44 as a negative reading having the value indicated, while a hyperopic condition will be indicated by a positive output.

A slope adjustment is required for patients whose pupils are too small to admit of all of the slit information focused thereon. Thus, for these patients a calibration in slope is necessary. It is also desirable to provide an output on the digital display means 44, not shown, for purposes of accommodating a chart recorder capable of recording one measurement each 30 milliseconds. In this manner, a trainer may obtain periodic real time records for the patient being trained.

The output of the sample-and-hold circuit 42 is also supplied through the conductors 52 and 53 to the tone generator means 45. The tone generator means 45 acts in the well-known manner to provide an output whose frequency varies as a function of the magnitude of the input voltage supplied thereto on the conductor 53. Thus, as the tone generator means 45 will receive a voltage value corresponding to the peak of each output scan of the sensor array means 14, it will be seen that the voltage supplied thereto on conductor 53 will increase in magnitude as the patient being trained increases from a myopic state of accommodation to an emmetropic state and from an emmetropic state to a condition of hyperopia. Therefore, assuming the tone generator means 45 provides an output of increasing frequency with increasing voltage, although any direct, inverse or exponential relationship could be employed, the frequency of the tone generator means 45 will increase, for instance, as a myopic patient learns to control accommodation through relaxation of the ciliary muscle and guides the accommodation level to an emmetropic state.

The output of the tone generator means 45 is selectively connectable through the switch means 54 to either the speaker means 46 or the headphones 47. In either case, tone information will be provided on a continuous basis to reflect the state of accommodation of the eye 15 being measured. Thus, if a myopic patient is being tested, the biofeedback information supplied through the speaker 46 or the headphones 47 will rise in tone as voluntary control of accommodation is achieved. The patient will strive to drive the tone upward, under the conditions indicated above, in a prompt, controlled manner as training progresses.

At some point during training, and this preferably will occur after the patient has demonstrated voluntary control of accommodation to a requisite degree in a dark environment, the instructor will selectively actuate the visual acuity array 12. This is done through activation of an appropriate one of the switches on the target select 30 to energize an appropriate one of the LED or LCD devices associated with the columns 21—24. When this occurs, radiation from the Snellen 21—24 characters on an energized one of the columns 21—24 will be projected according to the Badal principle through a lens means 9 and the first beam splitter means 10 on to the plane of the retina of the eye. Under these circumstances, the patient will discern the Snellen characters in an appropriate corner of what is being viewed.

In training a myopic patient, the column 21 would first be enabled, depending upon the state of the myopic condition, to enable the patient to attempt to extend his ability to drive the tone up in the presence of the character information AZWP which is now in his view. Assuming that the patient started with a 4 diopter condition, these characters would initially appear blurred. Therefore, the patient would have to overcome the tendency to lock the ciliary muscle in the presence of blur which increases the blur condition, and instead drive the tone up and in so doing render these characters clear. This would continue until the patient's voluntary control of accommodation was fully established or reestablished with the blur cue information present.

The instructor then may increase the ambient lighting in the room through the use of a dimmer switch or the like to restore a portion of the accommodation convergence reflex until voluntary control of accommodation under these circumstances was demonstrated. This could be done with or without a blur target being present, but it is preferred that these elements first be alternated and then combined to insure a full extension of the voluntary control of accommodation being learned.

Thereafter, the instruction would go to the next blur target associated with the column 22 and proceed in the same manner outlined above. This would continue until all of the blur targets were employed in full illumination, or alternatively, until the patient demonstrated that no futher progression was available. In this regard, it should be noted that training objectives for various degrees of myopia, for example, must be established. Thus, if the patient initially has less than 4 diopters of correction, the goal in training should be complete correction to 20/20 vision. However, if the initial condition is between 4 and 10 diopters, the goal will be improvement of the condition and correction on a part-time basis through the use of glasses or the like. If more than 10 diopters of correction is initially required, the goal should be a marked reduction in prescription. These goals, however, will vary with the individual patient with factors such as age, motivation, time commitment, health factors, experience with relaxation techniques, visual environment and ocular considerations being of prime importance. Additional factors which are highly influential are home training procedures including relaxation techniques such as yoga or the like. The total number of training sessions will depend upon goals established for the patient as well as the factors noted above.

When a patient initially enters training, the condition of his vision is tested and the patient is advised of the results thereof. The patient is then provided with background concerning the focusing or ciliary muscle, together with a brief description concerning its location, the manner in which it controls the lens of the eye and the manner in which the focusing muscle per se is controlled by the nervous system. If the patient is myopic, it is indicated that this is a result of a spasm of the focusing muscle; while if the patient is hyperopic, it is indicated that he has an inability to contract the focusing or ciliary muscles.

It is indicated that either case results in blurred vision which some people can correct by relaxation and control of the ciliary muscle, but many cannot. Those who cannot generally receive corrective lenses which eliminate the blur temporarily, but due to the tendency to continually overfocus, blurred vision returns to begin the cycle of stronger and stronger glasses. As this is particularly the case where myopia or nearsightedness is involved, patients exhibiting nearsightedness are advised that it has been theorized that people exhibiting functional myopia are nearsighted because when they see something blurry, their response is to overfocus and this response makes the blur condition worse. The patient is also advised that people who do not become nearsighted are able to relax their focus if something is seen to be blurry, and through a relaxation of the focus, such persons are able to render the object clear. Such discussion may be augmented by asking the patient to recall when wearing glasses began and the events which have occurred since then.

Thereafter, the patient is shown the accommodation training system and it is explained that training is initially conducted in the dark in order to break the accommodation convergence loop and remove all stimuli to accommodation. It is also explained that when the patient is placed in an operational relationship with the training system, no object will be perceived so that no blur cue to accommodation will be present. Subsequently in the training, each of these elements will be reintroduced. In this manner, it is explained, that training accomplishes relaxation of the tonus of the ciliary muscle and will enable the patient to learn voluntary control over accommodation. Once learned, a distant object which initially appears blurry will be rendered clear through voluntary control of accommodation by the patient as he will have learned an appropriate response mechanism to a blur cue and will no longer react by automatically overfocusing.

It is further explained that the training system measures the focus of the eye 33 times a second, and for each of these measurements, a tone will be produced which is proportional to the focus of the eye. The range of the tone is then demonstrated and, if desired, a particular subrange therein will be selected by the patient as the range to which the patient is most sensitive. It is explained that the tone serves to directionalize response to a blur condition, and through attention to the direction of the change in frequency or pitch of the tone, i.e., low to high or high to low, the patient will learn the proper reaction to a blur condition rather than automatically overfocusing in response thereto.

Thus, in the case of a myopic patient, it is explained that when the tone is relatively low it is indicative that the eye is everfocusing, and the goal of the training is for the patient to make the tone rise in frequency to as high a value as possible. When the tone is quite high, it is indicative that the ciliary muscle has been relaxed, is not in spasm, and under these conditions, a marked reduction in nearsightedness will obtain.

It is further explained that the training will be conducted using only one eye at a time since the nervous system control for each eye is the same. For this reason, the patient may patch one eye during training if so desired. The patient is then requested to seat himself at the end of the instrument table and look down the optical tube of the optometer. The patient will then either bite down on a bite plate or put his head in a head-and-chin rester while continuing to look into the optometer while the instructor conducts the alignment procedure.

The patient is aligned with the optometer in the manner described above in such manner that the center of the pupil is aligned with the axis A—A' so that image radiation from the slits is imaged on the plane of the pupil. This is done by illuminating the plurality of LED devices 17 through switch means not illustrated in FIG. 1. The bite bar, head-and-chin rester and/or optics are then adjusted horizontally and vertically until the projected ring associated with the plurality of LED devices 17 is imaged on the iris and concentric with the pupil. The patient will thus be placed in necessary alignment with the optometer and the propriety of such alignment may be checked by observing the CRT display 41 to ascertain whether a peak having a requisite voltage level is present. The instructor is aware of the condition of the patient so that the nature of the peak to be obtained on the CRT display 41 is known. Should the CRT display 41 indicate that alignment is not proper, fine adjustment may be achieved through further variations in the horizontal and vertical positioning of the bite bar, head-and-chin rester or optics so that a maximum voltage peak is achieved at the CRT display 41. The alignment procedure outlined above is conducted each time a patient is mounted to the embodiment of the invention illustrated in FIG. 1. It has been found that the use of the plurality of LED devices for initial alignment quickly and easily allows the alignment procedure to be completed. Once the alignment procedure is completed, the plurality of LED devices 17 are deenergized by the instructor.

If it is assumed that this is the patient's initial session, the patient is told to attempt to cause the tone to assume as high a frequency as possible. After approximately 20 seconds, the patient is told to sit back and relax and is advised whether or not he has been successful in relaxing focus. The instructor has observed the status of the patient's focusing and accommodation during the initial interval either by watching the CRT display 41 or the digital readout associated with the digital display 44 which provides an output directly in diopters or units of focus.

If the patient has relaxed focus, training in the foregoing manner is allowed to continue employing a training cycle of 15 seconds followed by approximately 15 seconds of rest with the eyes closed. These cycles continue for several minutes until the patient is stopped by the instructor or feels a burning sensation in the eye. The burning sensation in the eye is acute spasm of the ciliary muscle and the patient is told to avoid this result which occurs typically when the patient tries too hard. The patient is told that when this occurs, the eyes should be closed. Under these conditions the patient is allowed to rest for several minutes. When the instructor notices two consecutive accommodative levels on the CRT display 41 or the digital display 44 which are less than the previous level, the patient is also told to rest by closing the eyes.

Under conditions where the patient has not successfully relaxed his focus during the initial training interval, the patient is told to attempt to drive the tone up by opening his eyes to a greater extent. Additionally, the patient is told not to try to either change anything volitionally or to attempt to focus on anything which might be in his field of vision, such as the glow associated with the infrared source 3. Once the patient gains some success in causing the tone to increase in frequency, the instructor advises the patient to rest. Approximately 30 seconds of rest are allowed after each period where the patient attempts to increase the frequency of the tone through a heightening of the degree to which the eye is open.

Training will continue for approximately 20 minutes under conditions where the patient begins to willfully raise the frequency of the tone being fed back either through relaxation techniques which are developed without assistance on the instrument, or through the technique of increasing the degree to which the eye is open. In the course of this 20 minute period, the normal patient will develop two sensations in the eye. A burning sensation associated with an overfocusing response or spasm of the ciliary muscle is developed which the patient is told to avoid. The second sensation is a dilation sensation which is associated with the relaxation of the ciliary muscle. The patient is told to practice the dilation sensation or the feelings associated therewith even when not involved in a training.

When the state of perceiving these two sensations has been reached, the patient is allowed to train without verbal instructions from the instructor concerning eye openings and closings until such time as the instuctor notes that the patient is tiring through reduced readings at the digital display 44 or the CRT display 41. Most patients can usually train for approximately 10 minutes without rest under these conditions. After this training interval, the patient is provided with approximately 10 minutes rest time and training is continued for additional 10 minute intervals, or whatever the patient may comfortably accept, for the remaining portion of a one hour training session associated with the patient's initial training session.

At the conclusion of this initial training session, the patient is told of the progress made during the session. In virtually every case substantial progress does occur. Alternatively, the patient is removed from the embodiment of the invention illustrated in FIG. 1 and requested to read a standard Snellen eye chart where the patient's progress during the initial session is rendered manifest.

The patient is scheduled for further training sessions which are optimumly spaced at intervals of several days, however, under normal circumstances training intervals should not exceed one week. During typical one-hour or half-hour training sessions, four training periods will occur. The first period is a warming up period and the patient will normally exhibit a mild amount of success in driving up the frequency of the tone through relaxation of the ciliary muscle. The second period will exhibit the patient's best results and it is often desirable, at the completion of this period, to measure the patient's visual acuity and refraction on a standard Snellen eye chart. The third period is usually somewhat less successful than the second period, while the fourth period may have some good cycles of relaxation, but not many, and is characterized by easy fatigue.

During each training session, it is explained to the patient that training has two specific goals. The first is for the patient to learn voluntary control of accommodation so that through this muscular experience, vision can voluntarily become cleared or blurred. Thus, by decreasing the tonus of the ciliary muscle the patient may reduce myopia, while through increasing the tonus a patient may reduce hyperopia.

The second goal is to cause the improvement achieved during each training session to persist. In this regard, it is explained that the improvement obtained during a first training session may only last for a few hours while after a sixth or seventh training session, the improvement will persist for several days. The objective of the learned muscular experience is to cause the improvement to persist on a continuous basis.

Once the patient has come to know the feeling of dilation through which the output tone of the invention is caused to increase, training will frequently include an exercise. In such exercise, the patient is told to close the eyes and then open the eyes and try to drive the tone up as quickly as possible until a plateau is reached. Once this plateau is reached, the patient is requested to again close his eye and to continue this cycle for several minutes. During such training intervals, a successive increase in the frequency of each plateau reached is sought and a rest period is provided when the level of each plateau reached begins to decrease.

From the outset it is explained to the patient that the initial portions of biofeedback training are performed in the dark for purposes of stripping away all influences which might detract from the patient being able to control accommodation so that the appropriate muscular experience may be learned. Once this has been learned, however, it is necessary to generalize the training to a more conventional environment. For this purpose, the ambient lighting conditions will slowly be increased and periodically Snellen or eye chart characters will be introduced into the field of view of the training instrument to thus enable the patient to generalize the control being learned. This, in effect, is done once the patient begins to achieve accommodation levels which represent a very substantial improvement over the patient's entry levels. In this regard, it should be noted that the instructor will keep records of levels reached during each training session as indicated at the digital display 44.

Generalization from a dark environment in which an absence of all stimuli other than volitional control is present is performed, in accordance with the methods of the instant invention, through two independent techniques which are initially introduced separately and thereafter may be combined. More particularly, an increase in the ambient light level where the training is being conducted will act, as aforesaid, to reintroduce both stimuli to accommodation and the accommodation convergence reflex. Similarly, when reduced Snellen characters are introduced into a patient's field of vision, the overfocusing reaction to blur will again manifest itself. Hence, the voluntary control over accommodation which the patient has learned must be capable of being implemented in spite of the presence of such blur cues. An increase in the ambient light level in the training environment is introduced through a turning up of a dimmer switch or the like in the training room, while the introduction of blur cue information is introduced through the Badal optometer side channel associated with the visual acuity array 12, as aforesaid.

Generalization is introduced into the training by initially testing the patient's sensitivity to each form of generalization. More particularly, once the patient is ready for generalization, the instructor will elect to either increase the ambient light in the training environment to thereby restore stimuli to accommodation and the accommodation convergence reflex, or introduce a blur cue image through the use of the Badal side channel. As each effect is introduced, the instructor will note the patient's sensitivity by viewing the digital display means 44, as the patient continues to control his accommodation in the manner which was outlined above.

Whichever effect results in the greatest sensitivity in the patient is reserved and the effect for which less sensitivity is demonstrated is initially employed to generalize the training. Thus, if, as in the usual case, greatest sensitivity occurs as a result of placing blur cue information into the field of vision, the ambient light level in the training room is slowly brought up while the patient continues to control accommodation in the manner outlined above.

This is done until an ambient light level is reached which has a substantial effect on the results being achieved by the patient. Once this level is reached, the patient is allowed to practice at length with this level present. If the patient cannot quickly, voluntarily control his accommodation in the presence of the ambient light level imposed, this level is noted and thereafter the patient is again allowed to train for a period in a dark environment. Return to the noted ambient level is thereafter initiated and this procedure continues until such time as the patient demonstrates that adequate voluntary control over accommodation may be maintained despite the presence of the ambient light level introduced. Thereafter, the ambient light level is again increased and this continues typically until the patient demonstrates adequate control over accommodation under full ambient lighting conditions. Return to dark conditions, however, periodically occur so that continued improvement in the patient's voluntary control over accommodation can occur through the patient's continuously reaching higher levels in the biofeedback frequency returned and the diopter level reduction indicated at the digital display 44.

After one of the generalization techniques has been introduced into the training and completed to a successful degree, this technique is continuously introduced on a periodic basis into the training cycle. However, the other technique is also separately introduced and voluntary control of accommodation practiced. Thus, under the conditions here being discussed, the first technique being utilized was an increase in the ambient light level in the training room.

Once the patient has demonstrated proficient control over accommodation in the presence of this condition, a return to a dark environment will occur and blur targets will be selectively introduced. Thus, for instance, if training of a myopic patient is occurring, the target select 30 will be activated in such manner that the blur target 25 illustrated in FIG. 3 will be projected into the patient's field of view. Assuming that the patient's initial condition was such that more than 3 diopters of correction were required, the patient will be allowed to train with the blur target 25 in his field of view until such time as voluntary control over accommodation is demonstrated to an adequate degree with this blur target in place. Again, periodic return to a dark environment will occur so that the patient may continue to improve control.

This is continued for the remaining blur targets 26, 27 and 28 until an adequate level of accommodation is demonstrated with each of the blur targets in the manner outlined above. However, this assumes that the patient's training has reached a level where the relaxation of the ciliary muscle available to the patient is sufficient so that a viewing of an image with zero correction is available.

Once the patient has demonstrated adequate control over accommodation in the presence of blur targets and in the presence of an increased ambient light in the training environment, both techniques are introduced into the training. This is done on a combined, but graduated, basis to enable the patient to fully generalize the voluntary control over accommodation which has been learned. This, again, will continue together with periods of training in a dark environment until the voluntary control of accommodation which has been mastered by the patient has reached a peak which the patient can no longer better. The peak should also be maintainable in the presence of a normally lighted environment and with blur cue stimuli which are associated with the maximum reduction in correction of the patient. Where the patient had entered training with less than 4 diopters of correction required for normal vision, it is typical that full correction to 20/20 vision will be obtained. However, where the initial correction required was between 4 and 10 diopters, correction to a situation of glasses on a part-time basis is generally available. Where, however, the patient initially required more than 10 diopters of correction, only a reduction in the patient's prescription will typically be achieved. However, it will be appreciated by those of ordinary skill in the art that under any circumstances, a marked improvement in visual acuity is achieved.

MATTER ADDED BY THIS CONTINUATION-IN-PART

The infrared optometer employed for performing accommodation training, as described in connection with FIG. 1, was configured to principally detect retinal reflections from the eye being measured. Thus, as stated above, the lens means 8, described as an 88 millimeter lens, was positioned at an appropriate distance to eliminate corneal and lenticular reflections. Thus, as was described in connection with FIG. 1, lens means 8 was positioned 44 millimeters from the axis A—A and 105 millimeters from the sensor array 14 due to the length of the tube 13. When this is done, image radiation being sensed at the sensor array 14 tends to be somewhat insensitive to eye position since corneal and lenticular reflections are attenuated. The arrangement, however, is extremely sensitive to retinal reflections and hence is highly efficient and precise for purposes of measuring accommodation.

Lens/distance configurations may, however, be selected which provide a substantial component of corneal reflection at the sensor array 14. When this is done, the accommodation measured as a function of retinal reflection is less pronounced as the same is degraded. However, the optometer is rendered highly sensitive to eye position and may be employed as an eye position monitor enabling the same to be utilized in the treatment and correction through training of strabismus, eccentric fixation, nystagmus and related eye position disorders.

Thus, if the lens 8 is made stronger, it is displaced to a position closer to the axis A—A' or a second lens is used in conjunction with lens 8 to effectively shorten its focal length, the sensor means 14 will no longer reside at the focal point for retinal reflections. This will result in a degradation of signals obtained from the sensor array 14 as a result of retinal reflections.

However, a substantially stronger component of corneal reflection is superimposed thereon.

Those of ordinary skill in the art will appreciate that retinal reflection occurs from the back surface of the eye, while corneal reflection occurs from a front surface of the eye. Further, the eye essentially rotates around the center of those two points. Therefore, as each of the slits 18 and 19 is focused on the plane of the pupil of the eye 50 two entrance pupils, one for each slit, will be formed on the plane of the pupil of the eye and for each entrance pupil a corneal and retinal reflection will occur.

If the lens 8 is made stronger so that radiation from corneal reflection and somewhat degraded retinal reflection is imaged on the sensor array 14, the magnitude of the signal, as well as the location of the same on the sensor array 14, will be dispositive of the position of the eye and convey highly accurate information with respect thereto. Thus, under these conditions the highest readings will be obtained when the eye is properly aligned with the axis A—A' while lower readings are obtained anytime the eye is off axis with respect thereto.

The ability to make very precise measurements of eye position allows the system to be employed to train strabismus, eccentric fixation, nystagmus as well as other occular motor dysfunctions. For instance, in strabismus the patient typically has one eye that usually turns in, although a turned out or in the up or down direction is also not uncommon. The other eye will typically be straight. In eccentric fixation a turning of one eye results in image radiation being focused off the fovea which is the portion of the retina in the central 2° of the eye. Since the fovea has all the cones that provide sharp vision (20/20), image radiation focused off the fovea, even to a minor degree, results in vision of 20/200 Snellen acuity. Nystagmus is characterized by jerky motions of the eye which typically have metes and bounds which caude the eye to rotate from its central position where the axis of the eye would be aligned with the axis A—A, for instance, to a turned in, turned out, or turned up or turned down condition Hence, for each of these conditions, precisely monitoring the position of the eye and training a patient to control position is a highly effective form of treatment.

Figure 5:
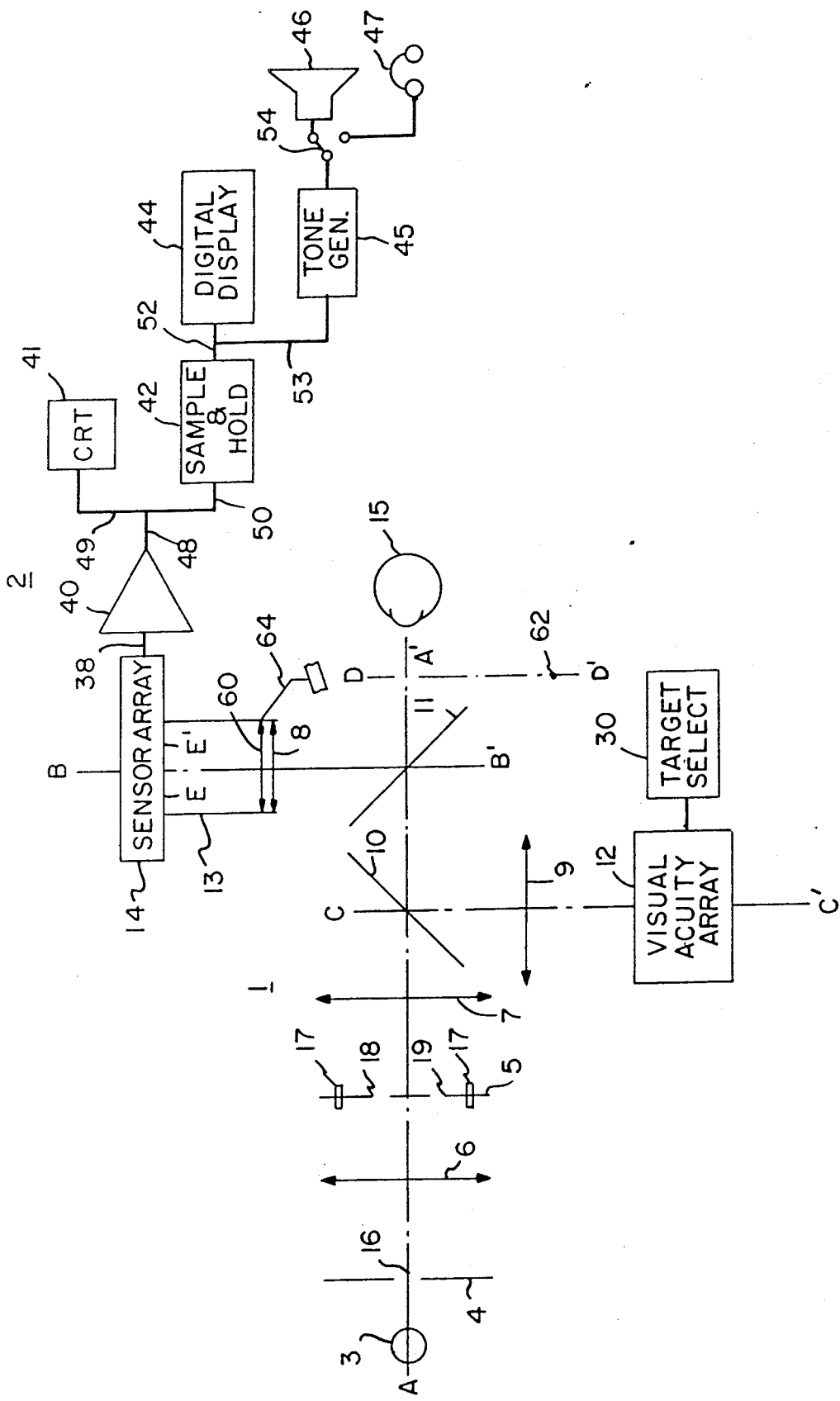
FIG. 5 is a modification of the system of FIG. 1 which is described in the portion of this specification entitled "Matter Added By This Continuation-in-Part" for monotoring and training eye position under clinical conditions.

Referring now to FIG. 5 there is shown a modification of the system of FIG. 1 suited to monitoring and training eye position under clinical conditions. Since the system illustrated in FIG. 5 is highly similar to that described in detail in connection with FIG. 1, common reference numerals and the like have been utilized therein to designated previously described common structure and the description of such previously structure will not be reiterated.

The system illustrated in FIG. 5 comprises an optometer portion 1 and an electronic portion 2 wherein the electronic portion 2 is precisely the same as that described in connection with FIG. 1. The optometer portion 1, however, has been modified to a minor degree by the addition of lens means 60 and LED 62. The function of the lens means 60 is to increase the strength of the resulting combination of the lens means 8 and 60 so that sensor array 14 is no longer at the focal point for retinal reflections from the eye 15. The lens means 60 is preferably mounted on a hinge 64 so that lens 60 may be swung into the operative position illustrated in FIG. 5 in a first position and rotated therefrom by operation of hinge 64 to a location displaced from optical axis B—B whereupon the optometer operates in the precise manner described in connection with FIG. 1. With the lens means 60 in the position shown, the optometer portion 1 is modified so that a combination of corneal reflection and retinal reflection is imaged on the sensor array 14 thereby making the optometer portion 1 highly sensitive to eye position. When the lens means 8 takes the form of an 88 millimeter lens axially displaced from axis A-A' by 44 millimeters, as described above, the lens means 60 may preferably take the form of an 18 millimeter lens which, in the engaged position shown, is positioned adjacent to lens means 8. The lens means 60, like lens means 8, may take the form of an achromatic doublet, condensing lens. Those of ordinary skill in the art, however, will appreciate that the focal lengths set forth are merely exemplary and a wide range is available. In addition, while use of a second lens means 60 has been illustrated herein, replacement of lens 8 with a single lens for purposes of rendering the optometer portion an eye position monitoring device is readily available or, alternatively, lens means 8 may be displaced closer to the optical axis A-A' to achieve the same result in rendering the optometer portion 1 sensitive to corneal reflection and somewhat degrade retinal reflection so that the radiation imaged thereon represents a combination of radiation reflected from the cornea and the retina. Those of ordinary skill in the art will further appreciate that in the exemplary embodiment of the instant invention set forth in connection with FIG. 1, the sensor array 14 is typically approximately one half of an inch long. Under the circumstances imposed in FIG. 5, while two slits 18 and 19 are focused on the plane of the pupil of the eye 15, the sensor array means 14 is not sufficiently long to receive corneal reflections and retinal reflections from both entrance slits at the pupil with the stronger lens combination of 8 and 60 being employed. This, however, is an appropriate result since image radiation corresponding to both retinal reflection and corneal reflection from a single entrance slit on the pupil is just as useful in the monitoring of eye position. However, should it be desired to monitor reflections from both entrance slits on the pupil, a somewhat longer sensor array means 14 may be employed.

With the addition of the lens means 60 in FIG. 5, those of ordinary skill in the art will appreciate that radiation representing a combination of radiation reflected from the retina and the cornea will be imaged upon the sensor array 14. This typically, when viewed on the CRT 41, will take the form of a narrow pulse whose magnitude and location along a horizontal axis will be a function of the position of the eye and, more particularly, the alignment of the axis of the eye 15, i.e. front to back, with the optical axis A-A' of the optometer portion 1. As aforesaid, since the eye tends to rotate about its center, reflections from a non-aligned eye, i.e. one misaligned towards the left (inward direction for a right eye) will produce corneal reflections from a position to the left of the axis A-A' and retinal reflections from a position to the right of the axis A-A'. The magnitude of the narrow pulse produced on the cathode ray tube 41 will be maximized when the eye is aligned with the axis A-A' and reduced as a direct function of the degree of misalignment. Further, while an aligned eye which has relaxed accommodation will produce a maximum magnitude pulse on the cathode ray tube 41, since radiation from retinal reflections is degraded by the arrangement of FIG. 5, the same will not be highly sensitive to conditions of accommodation.

It has also been noted that the amount of light needed for accurate measurement of retinal reflection is somewhat greater than for that required to accurately measure corneal reflection. Hence, when the lens means 60 is in place for purposes of measuring corneal reflection and retinal reflection in the manner illustrated in FIG. 5 by the position of the hinge means 64 shown, a reduction in the radiation output by source 3 is appropriate. While such reduction in the amount of radiation employed to measure corneal reflection may be obtained by reducing the power supplied to the source 3 or utilizing a neutral density filter along axis A-A' or B-B', it has been found that a simple solution to this problem may be obtained through the use of a neutral density coating on the lens means 60. Thus, without further adjustment to the source 3 or the insertion of any additional filters or the like within optic paths A-A' or B-B' the use of a neutral density coating on the lens means 60 results in full magnitude radiation when lens means 60 is out of the optic path and a reduction in the radiation when lens means 60 is present within the optic path for purposes of measuring corneal reflection.

The luminescent dot 62 may be provided by a single LED and functions, as shall be seen in greater detail below, as a fixation point for the fixating or straight eye in treating strabismus. The LED 62 is positioned at the front of the optometer in such manner that when the eye to be treated is aligned with axis A-A', the fixation LED 62 is positioned a distance corresponding to the inter-pupillary distance from the axis A-A' so as to be opposite the fixating or non-turning eye. In actuality, an LED may be mounted on a displaceable scale so that the patient's pupilatory distance, i.e. normally averaging 65 millimeters, may be measured and the LED 62 displaced from axis A-A' by this distance. Since either a patient's left or right eye may be treated for strabismus, the LED 62 may also be arranged to rotate about axis A-A' so the same may be appropriately positioned for the fixating eye regardless of whether the left or right eye is being treated. Alternatively, a row of LED devices may be positioned along the axis D-D' and after the patient's pupilatory distance is measured the appropriate LED device in the appropriate direction may be selectively illuminated, as shall be seen below, during the desired portion of a strabismus training session.

When the optometer 1 illustrated in FIG. 5 is being employed for accommodation training and the like, it will be appreciated that the lens 60, through the action of the hinge means 64, is positioned out of the optic path and away from axis B-B'. However, when it is desired that corneal reflection be measured with retinal reflection in such a manner that the retinal reflection is somewhat degraded so that corneal reflections are imaged on the sensor array 14, lens 60 is rotated into the optic path in the manner illustrated in FIG. 5 so it is centrally disposed along the axis B-B'. Due to the neutral density coating on the lens means 60, as aforesaid, the magnitude of radiation imaged on the sensor 14 will be somewhat reduced in the same manner as if the output of source 3 were reduced.

Those of ordinary skill in the art will now appreciate that with the lens 60 in the position illustrated in FIG. 5 corneal reflection and retinal reflection is measured by the sensor array 14. With the eye in an aligned position and accommodation relaxed, the sensor array 14 will provide a maximized output which will be represented on a cathode ray tube 41 as a narrowly defined pulse centered on an axis and have a maximum value for the patient being treated. As a result, the tone generator will output the highest frequency within the range selected. As accommodation is increased, the pulse shown on CRT 41 will be reduced in magnitude. However, its position along the abscissa will remain the same. When the eye turns about its central axis, corneal reflection will be markedly reduced and the position of the radiation reflected from the cornea will shift along the sensor array. Hence, if the eye being measured is not straight, i.e. aligned with axis A-A', a reduced and shifted pulse will be presented on the cathode ray tube 41. Thus, both with increased accommodation or a non-aligned condition of the eye the tone output by tone generator 45 will be reduced in frequency. Further, while accommodation is not highly sensitive to eye position, corneal reflection is in essence a direct function of the alignment of the eye and hence is markedly responsive to the position of the eye. Therefore, with the lens 60 in place in the manner illustrated in FIG. 5, the tone output by the tone generator 45 will vary substantially as a function of the aligned or non-aligned position of the eye 15.

Strabismus is a condition where one eye, the fixating, tends to look straight ahead while the other eye turns in, out, up or down, wherein an in or out condition is the most prevalent. In treating a condition of strabismus the lens 60 is placed in the condition illustrated in FIG. 5, the patient's pupilatory distance is measured, the turning eye is located in the position of eye 15 (along axis A-A') and the LED 62 is placed opposite the fixating eye but not illuminated. Thus, for instance, if the patient's right eye turns in, right esotropia, the right eye is placed in the position of 15 aligned with axis A-A' through the use of the bite plate, or head and chin rester noted above, and the LED 62 is positioned opposite the left eye and spaced from the axis A-A' by the patient's pupilatory distance as measured. Once this has been done the optometer is energized and the patient is instructed to cause the tone or sound go as high in frequency as possible. To do this the patient effectively is rotating eye 15 around its center so as to align the cornea with the axis A-A' and hence increase the corneal reflection measured by the sensor array 14 due to the presence of the lens means 60.

Once the eye is properly aligned along axis A-A', a high level output will be produced by the sensor array 14 which will result in a high frequency tone being output by the tone generator 45 in precisely the manner described above. This frequency can be further increased by a relaxation of accommodation and, hence, a maximum frequency output tone will be produced by the tone generator 45 by an eye 15 aligned along the axis A-A' when such eye is non-accommodating. However, whether a particular patient being trained to overcome strabismus has an accommodation problem or not tends to be independent of the strabismus condition.

After the patient has mastered the technique of increasing the output of the tone generator 45 to its maximum, his eye tends to be aligned along the axis A-A'. Thereafter, the zero diopter stimulus in the visual accuity array 12 is energized by action of the target select means 30 in the manner described above. In addition, the left or normally fixating eye is covered and the patient is again requested to drive the tone up, so that the patient is trained to look at a zero diopter target which resides at optical infinity, while straightening the alignment of the eye. Once the patient obtains a feeling for the condition that is present when the eye being trained, here the right eye, is straight, the left eye or normally fixating eye is uncovered and the fixation target provided by the LED 62 is illuminated. The patient is then requested to superimpose the zero diopter stimulus provided by the visual accuity array 12 on the luminous dot or fixation target provided by the LED 62. When this result is obtained, the eyes are aligned with their optic axes parallel since the left eye is normally looking straight ahead at the luminous dot so that effectively the right eye is brought into alignment therewith at optical infinity.

As the right eye goes in and out of alignment, proportional changes in tone produced by the tone generator 45 will occur with the highest tone again being presented when alignment is achieved. By building an increased awareness in the patient of this experience, the patient will be able to maintain parallel alignment of the optic axes of the eyes outside of the environment of the training system illustrated in FIG. 5. In actual treatment of cases of strabismus, initial alignment of the eyes has been obtained by patients within a period of about 10 minutes. In employing the system illustrated in FIG. 5 for purposes of treating strabismus, it is sometimes desirable to change the visual accuity array 12 so that single Snellin characters are illustrated therein rather than the multiple characters shown in FIG. 4. This obviously makes centering of the fixation dot and the optical stimulus provided by the visual accuity array 12 more simple. Similarly, a common character may be used for each of the four stimuli illustrated and training of strabismus may be carried out at the zero, one, two and three diopter levels with training being initiated for the zero diopter target until such time as the patient acquires a real facility for achieving this end.

Eccentric fixation is a condition of the eye wherein image radiation is focused outside of the fovea. The fovea is the portion of the retina which is the central 2° of the eye and it is within the fovea that all cones which provide us with sharp 20/20 vision reside. Thus, if image radiation is focused off of the fovea, vision of 20/200 Snellen acuity will result. Eccentric fixation is a combination of a nervous and muscle disorder and hence readily admits of the training techniques set forth herein. When the diagnosis is eccentric fixation, the eye is not straight and as a result the misalignment of the eye will cause image radiation to be focused on a portion of the retina outside of the fovea. In addition, with a diagnosis of eccentric fixation by definition, the accommodation function of the patient is also bad. Hence, here, training takes the form of first aligning of the eye and thereafter accommodation training as set forth above is performed.

In training patients exhibiting eccentric fixation, the eye manifesting this problem is aligned with the optical axis A-A' of the system in the manner set forth above. If both eyes display this impediment, the worst eye is trained. For training eccentric fixators, the lens 60 is initially placed in the position shown in FIG. 5 and the fixation dot 62 is left in a disabled condition. The system is then energized and the patient is requested to drive the tone exhibited by the tone generator 45 as high as possible. This effectively is a straightening of the eye along the axis A—A and occurs in much the same manner described for strabismus with a rather sharp transition in frequency occurring when the off axis condition of the eye is corrected so that image radiation is placed onto the fovea. Once the patient has again learned the feeling of having his eye straight or aligned with the axis A-A' and is capable of achieving this result at will and maintaining it, accommodation training for that eye is then performed in the manner outlined above. In the case of eccentric fixators, this is quite important since, in the case of eccentric fixation the accommodation function of the patient is also basically impaired and hence training in this regard must be performed.

Nystagmus is a condition where the eye displays jerky movements from an aligned to a non-aligned condition. The non-aligned condition may be turned in, turned out, up or down with the turned in condition again being most prevalent. It too is a combination of a muscular and nervous condition which again may be readily overcome through biofeedback training techniques of the type described herein.

For nystagmus training the eye manifesting this condition is again aligned with the axis A-A', the lens 60 is placed in the position shown so that the sensor array 14 is rendered highly sensitive to the position of the eye and the fixation dot 62 remains unenergized. As will now be apparent, in the case of nystagmus, the output of the tone generator 44 will vary from a high frequency condition when the eye is in an aligned condition to a lower frequency tone when the eye is in a non-aligned condition with the frequency of the tone generator 44 shifting between these two conditions as the eye jerks from an aligned to a non-aligned condition. Thus, here, the patient is instructed to attempt to hold a tone at the high frequency condition or reduce the frequency of the shifts between the high frequency tone and the low frequency tone. Marked improvements can frequently be obtained within the first few minutes of training since the patient is suddenly provided with an auditory measure of the rate at which the eye jerks back and forth between an aligned and non-aligned condition. Once the patient is made aware of the feeling obtained for an aligned condition of the eye, as results from the training being employed, the nystagmus condition may be markedly improved in a relatively few training sessions.

In this regard, it should also be noted that the training is somewhat more simply perceived by the patient since here the object is to render the tone output by the tone generator 45 constant.

The system for performing accommodation training set forth herein is viewed as highly advantageous in that for the first time, apparatus and methods for clinically enabling such training to be extended to patients seeking an improvement in visual acuity is provided. Those of ordinary skill in the art will recognize that while variations and alternatives are available in both the apparatus and methods set forth to accommodate the requirements or preferences of specific situations, the integrated methods and training techniques set forth herein provide a generalized approach to training which fully admit of such variations.

Furthermore, while the invention has been disclosed in regard to a rather specific embodiment thereof, it will be apparent to those of ordinary skill in the art that the teachings herein and the apparatus described may be readily varied to suit specific design preferences or training situations and may well be varied as a function of the age and condition of various patients.

For instance, in addition to using retinal reflection to measure the refraction of an eye and corneal reflection to measure eye movements, the present invention may be employed in measuring crystalline lens reflections to measure refraction and/or eye movements. More particularly, lens reflection, known as the Purkinje Images (P.I.), may be utilized for this purpose. Thus, the anterior lens reflection, known as the Third P.I., and the posterior lens reflection, known as the Fourth P.I., and specifically the separation therebetween as measured at the sensor, may be employed to measure refraction.

To utilize such reflections to measure refraction and/or eye movements, the double slit means 5 would be removed from the optical system to allow an image of the single slit means 4, acting as the source, to be formed as the Third and Fourth P.I.'s. These images would then be reflected by the beam splitter means 11 and focused on to the sensor. To measure the refraction of the eye, the separation of the P.I.'s on the sensor would be noted. As the eye increases its accommodation, the P.I.'s would move away from each other, while as the eye decreases its accommodation, the P.I.'s move toward one another.

Alternatively, the size of the P.I.'s would be measured since as the eye increases its accommodation, the Third P.I. would decrease in size and the Fourth P.I. would increase in size. Conversely, during the process of decreasing accommodation, the Third P.I. increases in size and the Fourth P.I. decreases in size. To measure eye position, the distance between the Third and Fourth P.I.'s would also be noted. As the eye rotates in its socket, the distance between the Third and Fourth P.I.'s will vary. The greater the eye movement from the primary position (eye straight ahead), the greater the separation of the two images, assuming constant accommodation.

Thus, although the instant invention has been described in connection with a highly specific exemplary embodiment thereof, it will be understood that many modifications and variations thereof will be readily apparent to those of ordinary skill in the art. Therefore, it is manifestly intended that this invention be only limited by the claims and the equivalents thereof.

What is claimed is:

1. Ophthalmologic training apparatus comprising:
   optometer means for imaging radiation onto the plane of the pupil of an eye and measuring radiation reflected by the cornea and retina to directly measure the position of said eye as a function of radiation reflected by the cornea and retina of said eye, said optometer means providing outputs representing said position of said eye on a periodic basis and at a rate corresponding to a plurality of measurements each second; and
   audio means responsive to each output of said optometer means for producing biofeedback tone information having a frequency representative of the position of an eye being measured.

2. The ophthalmologic training apparatus according to claim 1 wherein said optometer means includes sensor means for receiving radiation reflected from said eye and providing outputs on a periodic basis which vary as a function of said radiation received and lens means for imaging radiation reflected from said eye onto said sensor means.

3. Ophthalmologic training apparatus comprising:
   optometer means for imaging radiation onto the plane of the pupil of an eye and directly measuring the position of said eye as a function of radiation reflected by the cornea and retina of said eye, said optometer means providing outputs representing said position of said eye on a periodic basis and at a rate corresponding to a plurality of measurements each second, said optometer means including sensor means for receiving radiation reflected from said eye and providing outputs on a periodic basis which vary as a function of said radiation received and lens means for imaging radiation reflected from said eye onto said sensor means, wherein said lens means comprises;
   first lens means for imaging radiation reflected from a retinal image onto said sensor means, said first lens means having a predetermined focal length, and
   second lens means for imaging radiation reflected by said cornea of said eye onto said sensor means, said second lens means having a shorter focal length than said predetermined focal length; and
   audio means responsive to each output of said optometer means for producing biofeedback tone information having a frequency representative of the position of an eye being measured.

4. The ophthalmologic training apparatus according to claim 3 additionally comprising means for selectively placing said second lens means in optical communication with said first lens means, said first and second lens means when in optical communication having a focal length shorter than said predetermined focal length and imaging radiation reflected by said cornea and from said retinal image onto said sensor means.

5. The ophthalmologic training apparatus according to claim 3 wherein said second lens means has a neutral density coating thereon which acts to attenuate radiation reflected by said cornea and imaged onto said sensor means.

6. The ophthalmologic training apparatus according to claim 5 additionally comprising means for selectively placing said second lens means in optical communication with said first lens means, said first and second lens means when in optical communication having a focal length shorter than said predetermined focal length and imaging radiation reflected by said cornea and from said retinal image onto said sensor means.

7. The ophthalmologic training apparatus according to claim 4 wherein said means for selectively placing said second lens means in optical communication with said first lens means includes hinge means for optically inserting said second lens means intermediate said first lens means and said sensor means.

8. The ophthalmologic training apparatus according to claim 7 wherein said second lens means has a neutral density coating thereon which acts to attenuate radiation reflected by said cornea imaged onto said sensor means.

9. The ophthalmologic training apparatus according to claim 8 additionally comprising fixation dot means for selectively supplying fixation information to an eye not receiving radiation from said optometer means.

10. The ophthalmologic training apparatus according to claim 9 additionally comprising side channel means for selectively placing blur cue information onto said optometer means for projection by said optometer means onto the retinal of said eye during training to permit training to selectively occur in the presence of a focusing target.

11. The ophthalmologic training apparatus according to claim 9 additionally comprising:
sample-and-hold means connected to said optometer means for directly receiving each output provided thereby, said sample-and-hold means storing each output received from said optometer means and producing an output signal representative of the peak level of each output stored, said sample-and-hold means acting to store each output received from said optometer means until a succeeding output is received to provide a continuous output signal having a magnitude representative of the peak level of the last output received from said optometer means;
frequency convertor means for producing tone information which varies as a function of said output signal produced by said sample-and-hold means, said frequency convertor means being connected to directly receive said output signal produced by said sample-and-hold means; and
transducer means for receiving said tone information produced by said frequency convertor means and producing continuous, audible information therefrom to immediately indicate the condition of an eye being measured.

12. A method of eye position training comprising the steps of:
projecting radiation onto the plane of the pupil of an eye in a dark environment;
imaging radiation reflected by the cornea of said eye upon sensor means to directly measure the position of said eye as a function of radiation reflected by said cornea;
scanning said sensor means on a periodic basis to provide outputs representing the measured position of said eye, said scanning occurring at a rate corresponding to a plurality of measurements each second;
sampling each output provided by scanning and holding a value representative of a peak value of each output sampled until a succeeding output is produced;
continuously translating each value held to tone information having a frequency representative of said value held and corresponding to said measured position of said eye;
transducing said tone information into audible information to provide continuous biofeedback information to a patient being trained indicative of the current position of said eye; and
instructing said patient to cause said audible information to assume a preselected condition.

13. The method of eye position training according to claim 12 wherein said step of instructing is performed by advising said patient to cause said audible information to assume a constant frequency.

14. The method of eye position training according to claim 12 wherein after said patient has caused said audible information to assume said preselected condition, the following steps are performed:
imaging radiation reflected from the retina of said eye upon said sensor means to directly measure the refraction of said eye as a function of the retinal image;
scanning said sensor means on a periodic basis to provide outputs representing the measured refraction of said eye;
displaying each output provided;
sampling each output provided by scanning and holding a value representative of a peak value of each output sampled until a succeeding output is produced;
continuously translating each value held to tone information having a frequency representative of said value held and corresponding to said measured refraction of said eye;
transducing said tone information into audible information to provide continuous biofeedback information to a patient being trained indicative of the current state of accommodation of said eye;
monitoring indicia of each output displayed and the condition of the patient being trained; and
providing rest intervals for said patient in response to a spasm condition in said eye being measured or tiring of said patient as indicated by said indicia and condition monitored.

15. The method of eye position training according to claim 12 wherein after said patient has caused said audible information to assume said preselected condition, the following steps are performed:
patching the patient's eye which is not receiving projected radiation; and
selectively projecting zero diopter blur cue information onto the retina of the eye receiving projected radiation.

16. The method of eye position training according to claim 15 additionally comprising the steps of:
removing the patch from the patient's eye; and
illuminating a fixation point opposite the pupil of the eye from which the patch was removed.

17. The method of eye position training according to claim 16 additionally comprising the steps of instructing the patient to superimpose said fixation point on said zero diopter blur cue information.

* * * * *